US012773520B2

(12) United States Patent
Howell

(10) Patent No.: US 12,773,520 B2
(45) Date of Patent: Oct. 27, 2026

(54) APPARATUS AND METHOD FOR TIPPING RAPIDLY INSERTABLE CENTRAL CATHETERS (RICC)

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 803 days.

(21) Appl. No.: 18/098,059

(22) Filed: Jan. 17, 2023

(65) Prior Publication Data

US 2023/0233796 A1 Jul. 27, 2023

Related U.S. Application Data

(60) Provisional application No. 63/301,886, filed on Jan. 21, 2022.

(51) Int. Cl.
*A61M 25/00* (2006.01)

(52) U.S. Cl.
CPC .... *A61M 25/0009* (2013.01); *A61M 25/0026* (2013.01)

(58) Field of Classification Search
CPC .......... A61M 25/0009; A61M 25/0026; A61M 25/007; A61M 25/0606; A61M 2025/0004; B29C 33/0022; B29C 33/0033
See application file for complete search history.

(56) References Cited

U.S. PATENT DOCUMENTS 1,013,691 A 1/1912 Shields
1,906,678 A 5/1933 Wappler
(Continued)

FOREIGN PATENT DOCUMENTS

EP 0730880 A1 9/1996
EP 2061385 A1 5/2009
(Continued)

OTHER PUBLICATIONS

PCT/US2022/047179 filed Oct. 19, 2022 International Preliminary Report on Patentability dated Apr. 23, 2024.
(Continued)

*Primary Examiner* — Galen H Hauth
*Assistant Examiner* — Baileigh Kate Darnell
(74) *Attorney, Agent, or Firm* — Rutan & Tucker LLP

(57) ABSTRACT

A Rapidly Insertable Central Catheter ("RICC") includes an access section formed of a first material, a catheter body section formed of a second material, and a dilator section disposed therebetween. The first material has a first durometer and the second material has a second, lesser durometer. The dilator section is formed of the first material, the second material, or a third material having a third durometer. The catheter body defines a primary lumen communicating with a primary lumen aperture disposed in a distal tip of the access section, a secondary lumen communicating with a secondary lumen aperture and a tertiary lumen communicating with a tertiary lumen aperture. The secondary lumen aperture and the tertiary lumen aperture can be disposed at an equal longitudinal length from the primary lumen aperture. The RICC can include intricate tip structures formed from different materials and can define a smooth abluminal surface.

12 Claims, 13 Drawing Sheets

FIG. 7C

(56) References Cited

U.S. PATENT DOCUMENTS 3,225,762 A 12/1965 Guttman
3,710,781 A 1/1973 Huthcins, IV et al.
3,890,976 A 6/1975 Bazell et al.
4,205,675 A 6/1980 Vaillancourt
4,270,535 A 6/1981 Bogue et al.
4,292,970 A 10/1981 Hession, Jr.
4,468,224 A 8/1984 Enzmann et al.
4,525,157 A 6/1985 Vaillancourt
4,577,637 A 3/1986 Mueller, Jr.
4,581,019 A 4/1986 Curelaru et al.
4,661,300 A 4/1987 Daugherty
5,004,455 A 4/1991 Greenwood et al.
5,017,259 A 5/1991 Kohsai
5,040,548 A 8/1991 Yock
5,057,073 A 10/1991 Martin
5,112,312 A 5/1992 Luther
5,120,317 A 6/1992 Luther
5,135,599 A * 8/1992 Martin .............. A61M 25/0028 604/523
5,167,623 A 12/1992 Cianci et al.
5,188,593 A 2/1993 Martin
5,195,962 A 3/1993 Martin et al.
5,207,650 A 5/1993 Martin
5,267,958 A 12/1993 Buchbinder et al.
5,295,970 A 3/1994 Clinton et al.
5,306,247 A 4/1994 Pfenninger
5,328,472 A 7/1994 Steinke et al.
5,350,358 A 9/1994 Martin
5,368,567 A 11/1994 Lee
5,378,230 A 1/1995 Mahurkar
5,380,290 A 1/1995 Makower et al.
5,389,087 A 2/1995 Miraki
5,439,449 A 8/1995 Mapes et al.
5,443,457 A 8/1995 Ginn et al.
5,489,271 A 2/1996 Andersen
5,573,520 A 11/1996 Schwartz et al.
5,645,528 A 7/1997 Thome
5,683,370 A 11/1997 Luther et al.
5,690,613 A 11/1997 Verbeek
5,718,678 A 2/1998 Fleming, III
5,772,636 A 6/1998 Brimhall et al.
5,810,789 A 9/1998 Powers et al.
5,885,251 A 3/1999 Luther
5,908,409 A 6/1999 Rinehart et al.
5,919,164 A 7/1999 Andersen
5,947,940 A 9/1999 Beisel
5,957,893 A 9/1999 Luther et al.
6,206,849 B1 3/2001 Martin et al.
6,332,877 B1 12/2001 Michels
6,475,187 B1 11/2002 Gerberding
6,551,290 B1 4/2003 Elsberry et al.
6,606,515 B1 8/2003 Windheuser et al.
6,716,228 B2 4/2004 Tal
6,726,659 B1 4/2004 Stocking et al.
6,819,951 B2 11/2004 Patel et al.
6,821,287 B1 11/2004 Jang
6,926,692 B2 8/2005 Katoh et al.
6,962,575 B2 11/2005 Tal
6,994,693 B2 2/2006 Tal
6,999,809 B2 2/2006 Currier et al.
7,025,746 B2 4/2006 Tal
7,029,467 B2 4/2006 Currier et al.
7,037,293 B2 5/2006 Carrillo et al.
7,074,231 B2 7/2006 Jang
7,141,050 B2 11/2006 Deal et al.
7,144,386 B2 12/2006 Korkor et al.
7,311,697 B2 12/2007 Osborne
7,364,566 B2 4/2008 Elkins et al.
7,377,910 B2 5/2008 Katoh et al.
7,390,323 B2 6/2008 Jang
D600,793 S 9/2009 Bierman et al.
D601,242 S 9/2009 Bierman et al.
D601,243 S 9/2009 Bierman et al.
7,594,911 B2 9/2009 Powers et al.
7,691,093 B2 4/2010 Brimhall
7,722,567 B2 5/2010 Tal
D617,893 S 6/2010 Bierman et al.
D624,643 S 9/2010 Bierman et al.
7,819,889 B2 10/2010 Healy et al.
7,857,788 B2 12/2010 Racz
D630,729 S 1/2011 Bierman et al.
7,909,797 B2 3/2011 Kennedy, II et al.
7,909,811 B2 3/2011 Agro et al.
7,922,696 B2 4/2011 Tal et al.
7,938,820 B2 5/2011 Webster et al.
7,967,834 B2 6/2011 Tal et al.
7,985,204 B2 7/2011 Katoh et al.
8,073,517 B1 12/2011 Burchman
8,105,286 B2 1/2012 Anderson et al.
8,192,402 B2 6/2012 Anderson et al.
8,202,251 B2 6/2012 Bierman et al.
8,206,356 B2 6/2012 Katoh et al.
8,372,107 B2 2/2013 Tupper
8,377,006 B2 2/2013 Tal et al.
8,454,577 B2 6/2013 Joergensen et al.
8,585,858 B2 11/2013 Kronfeld et al.
8,657,790 B2 2/2014 Tal et al.
8,672,888 B2 3/2014 Tal
8,696,645 B2 4/2014 Tal et al.
8,784,362 B2 7/2014 Boutilette et al.
8,827,958 B2 9/2014 Bierman et al.
8,876,704 B2 11/2014 Golden et al.
8,882,713 B1 11/2014 Call et al.
8,900,192 B2 12/2014 Anderson et al.
8,900,207 B2 12/2014 Uretsky
8,915,884 B2 12/2014 Tal et al.
8,956,327 B2 2/2015 Bierman et al.
9,023,093 B2 5/2015 Pal
9,138,252 B2 9/2015 Bierman et al.
9,180,275 B2 11/2015 Helm
9,265,920 B2 2/2016 Rundquist et al.
9,272,121 B2 3/2016 Piccagli
9,522,254 B2 12/2016 Belson
9,554,785 B2 1/2017 Walters et al.
9,566,087 B2 2/2017 Bierman et al.
9,675,784 B2 6/2017 Belson
9,713,695 B2 7/2017 Bunch et al.
9,764,117 B2 9/2017 Bierman et al.
9,770,573 B2 9/2017 Golden et al.
9,814,861 B2 11/2017 Boutillette et al.
9,820,845 B2 11/2017 von Lehe et al.
9,861,383 B2 1/2018 Clark
9,884,169 B2 2/2018 Bierman et al.
9,889,275 B2 2/2018 Voss et al.
9,913,585 B2 3/2018 McCaffrey et al.
9,913,962 B2 3/2018 Tal et al.
9,950,139 B2 4/2018 Blanchard et al.
9,981,113 B2 5/2018 Bierman
10,010,312 B2 7/2018 Tegels
10,065,020 B2 9/2018 Gaur
10,098,724 B2 10/2018 Adams et al.
10,111,683 B2 10/2018 Tsamir et al.
10,118,020 B2 11/2018 Avneri et al.
10,130,269 B2 11/2018 McCaffrey et al.
10,220,184 B2 3/2019 Clark
10,220,191 B2 3/2019 Belson et al.
10,265,508 B2 4/2019 Baid
10,271,873 B2 4/2019 Steingisser et al.
10,376,675 B2 8/2019 Mitchell et al.
10,675,440 B2 6/2020 Abitabilo et al.
10,806,901 B2 10/2020 Burkholz et al.
2001/0044594 A1 11/2001 Martin et al.
2002/0040231 A1 4/2002 Wysoki
2002/0107506 A1 8/2002 McGuckin et al.
2002/0198492 A1 12/2002 Miller et al.
2003/0036712 A1 2/2003 Heh et al.
2003/0060863 A1 3/2003 Dobak
2003/0088212 A1 5/2003 Tal
2003/0100849 A1 5/2003 Jang
2003/0153874 A1 8/2003 Tal
2003/0158514 A1 8/2003 Tal
2004/0116901 A1 6/2004 Appling
2004/0193093 A1 9/2004 Desmond
2004/0230178 A1 11/2004 Wu

(56) References Cited

U.S. PATENT DOCUMENTS

2005/0004554 A1 1/2005 Osborne
2005/0049552 A1* 3/2005 Holzapfel ......... A61M 25/1025 156/198
2005/0245882 A1 11/2005 Elkins et al.
2005/0245887 A1 11/2005 Olsen et al.
2005/0283221 A1 12/2005 Mann et al.
2006/0009740 A1 1/2006 Higgins et al.
2006/0116629 A1 6/2006 Tal et al.
2006/0129100 A1 6/2006 Tal
2006/0129130 A1 6/2006 Tal et al.
2008/0039796 A1 2/2008 Nakajima
2008/0045894 A1 2/2008 Perchik et al.
2008/0125744 A1 5/2008 Treacy
2008/0125748 A1 5/2008 Patel
2008/0262430 A1 10/2008 Anderson et al.
2008/0262431 A1 10/2008 Anderson et al.
2008/0294111 A1 11/2008 Tal et al.
2008/0312578 A1 12/2008 DeFonzo et al.
2009/0093670 A1 4/2009 Annest et al.
2009/0221961 A1 9/2009 Tal et al.
2009/0247868 A1 10/2009 Chesnin
2009/0270889 A1 10/2009 Tal et al.
2010/0191165 A1 7/2010 Appling et al.
2010/0256487 A1 10/2010 Hawkins et al.
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0144620 A1 6/2011 Tal
2011/0152836 A1 6/2011 Riopelle et al.
2011/0202006 A1 8/2011 Bierman et al.
2011/0251559 A1 10/2011 Tal et al.
2011/0270192 A1 11/2011 Anderson et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0209221 A1 8/2012 Patterson et al.
2012/0220942 A1 8/2012 Hall et al.
2012/0283640 A1 11/2012 Anderson et al.
2012/0316500 A1 12/2012 Bierman et al.
2013/0012924 A1 1/2013 Davis et al.
2013/0053826 A1 2/2013 Shevgoor
2013/0123704 A1 5/2013 Bierman et al.
2013/0158338 A1 6/2013 Kelly et al.
2013/0188291 A1 7/2013 Vardiman
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0094741 A1 4/2014 Bellisario et al.
2014/0100552 A1 4/2014 Gallacher et al.
2014/0155863 A1 6/2014 Walker et al.
2014/0180255 A1 6/2014 LeBlanc et al.
2014/0207052 A1 7/2014 Tal et al.
2014/0207069 A1 7/2014 Bierman et al.
2014/0214005 A1 7/2014 Belson
2014/0257111 A1 9/2014 Yamashita et al.
2014/0276432 A1 9/2014 Bierman et al.
2014/0276599 A1 9/2014 Cully et al.
2015/0080939 A1 3/2015 Adams et al.
2015/0112310 A1 4/2015 Call et al.
2015/0126930 A1 5/2015 Bierman et al.
2015/0148595 A1 5/2015 Bagwell et al.
2015/0190168 A1 7/2015 Bierman et al.
2015/0196210 A1 7/2015 McCaffrey et al.
2015/0224287 A1 8/2015 Bian et al.
2015/0283357 A1 10/2015 Lampropoulos et al.
2015/0297868 A1 10/2015 Tal et al.
2015/0320969 A1 11/2015 Haslinger et al.
2015/0351793 A1 12/2015 Bierman et al.
2015/0359549 A1 12/2015 Lenker et al.
2015/0359998 A1 12/2015 Carmel et al.
2016/0082223 A1 3/2016 Barnell
2016/0114124 A1 4/2016 Tal
2016/0220786 A1 8/2016 Mitchell et al.
2016/0220795 A1 8/2016 Korkuch et al.
2016/0325073 A1 11/2016 Davies et al.
2016/0338728 A1 11/2016 Tal
2016/0346503 A1 12/2016 Jackson et al.
2017/0035989 A1 2/2017 Gilman
2017/0035990 A1 2/2017 Swift
2017/0072165 A1 3/2017 Lim et al.
2017/0120000 A1 5/2017 Osypka et al.
2017/0128700 A1 5/2017 Roche Rebollo
2017/0172653 A1 6/2017 Urbanski et al.
2017/0239443 A1 8/2017 Abitabilo et al.
2017/0273713 A1 9/2017 Shah et al.
2017/0296792 A1 10/2017 Ornelas Vargas et al.
2017/0326339 A1 11/2017 Bailey et al.
2017/0333681 A1 11/2017 Di Caprio et al.
2017/0361070 A1 12/2017 Hivert
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0193042 A1 7/2018 Wilson et al.
2018/0296799 A1 10/2018 Horst et al.
2018/0296804 A1 10/2018 Bierman
2018/0339131 A1 11/2018 Muse et al.
2019/0015646 A1 1/2019 Matlock et al.
2019/0060616 A1 2/2019 Solomon
2019/0076167 A1 3/2019 Fantuzzi et al.
2019/0134349 A1 5/2019 Cohn et al.
2019/0255294 A1 8/2019 Mitchell et al.
2019/0276268 A1 9/2019 Akingba
2019/0321590 A1 10/2019 Burkholz et al.
2020/0016374 A1 1/2020 Burkholz et al.
2020/0030124 A1 1/2020 Bluecher et al.
2020/0094025 A1 3/2020 Wisman
2021/0069471 A1 3/2021 Howell
2021/0121661 A1 4/2021 Howell
2021/0121667 A1 4/2021 Howell
2021/0187245 A1 6/2021 Ishida
2021/0322729 A1 10/2021 Howell
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0001138 A1 1/2022 Howell
2022/0032013 A1 2/2022 Howell et al.
2022/0040447 A1 2/2022 Mewissen
2023/0126869 A1 4/2023 Sepulveda et al.
2023/0132903 A1 5/2023 Sepulveda et al.
2023/0233800 A1 7/2023 Howell et al.
2024/0091501 A1 3/2024 Howell
2024/0181210 A1 6/2024 Howell et al.
2024/0198042 A1 6/2024 Sepulveda
2026/0199633 A1 7/2026 Howell et al.

FOREIGN PATENT DOCUMENTS

EP 1458437 B1 3/2010
EP 2248549 A2 11/2010
EP 2319576 A1 5/2011
EP 2366422 A1 9/2011
EP 2486880 A2 8/2012
EP 2486881 A2 8/2012
EP 2486951 A2 8/2012
EP 2512576 A2 10/2012
EP 2152348 B1 2/2015
EP 3093038 B1 5/2019
EP 2260897 B1 9/2019
ES 2303546 T3 8/2008
GB 1273547 A 5/1972
WO 94/21315 A1 9/1994
WO 95/32009 A2 11/1995
WO 98/44979 A1 10/1998

(56) References Cited

FOREIGN PATENT DOCUMENTS

| | | | |
|---|---|---|---|
| WO | 98/53871 | A1 | 12/1998 |
| WO | 99/12600 | A1 | 3/1999 |
| WO | 99/26681 | A1 | 6/1999 |
| WO | 2003008020 | A1 | 1/2003 |
| WO | 2003057272 | A2 | 7/2003 |
| WO | 2003066125 | A2 | 8/2003 |
| WO | 2004037331 | A1 | 5/2004 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2023069553 | A2 | 4/2023 |
| WO | 2023081314 | A1 | 5/2023 |
| WO | 2023141112 | A1 | 7/2023 |
| WO | 2023146773 | A3 | 9/2023 |
| WO | 2024123925 | A2 | 6/2024 |
| WO | 2024129815 | A1 | 6/2024 |

OTHER PUBLICATIONS

PCT/US2023/083764 filed Dec. 13, 2023 International Search Report and Written Opinion dated Apr. 22, 2024.
U.S. Appl. No. 17/363,500, filed Jun. 30, 2021 Restriction Requirement dated Jul. 16, 2024.
U.S. Appl. No. 17/363,500, filed Jun. 30, 2021 Final Office Action dated Feb. 20, 2025.
U.S. Appl. No. 17/363,500, filed Jun. 30, 2021 Non-Final Office Action dated Sep. 4, 2025.
U.S. Appl. No. 17/969,626, filed Oct. 19, 2022 Non-Final Office Action dated Sep. 25, 2025.
U.S. Appl. No. 17/980,455, filed Nov. 3, 2022 Restriction Requirement dated Nov. 19, 2025.
U.S. Appl. No. 18/076,169, filed Dec. 6, 2022 Non-Final Office Action dated Aug. 8, 2025.
U.S. Appl. No. 18/076,169, filed Dec. 6, 2022 Notice of Allowance dated Dec. 5, 2025.
U.S. Appl. No. 18/081,480, filed Dec. 14, 2022 Non-Final Office Action dated Sep. 17, 2025.
U.S. Appl. No. 18/098,052, filed Jan. 17, 2023 Restriction Requirement dated Dec. 5, 2025.
PCT/US2022/047179 filed Oct. 19, 2022 International Search Report and Written Opinion dated Apr. 18, 2023.
PCT/US2022/048881 filed Nov. 3, 2022 International Search Report and Written Opinion dated Mar. 31, 2023.
PCT/US2023/010972 filed Jan. 17, 2023 International Search Report and Written Opinion dated May 30, 2023.
PCT/US2020/048583 filed Aug. 28, 2020 International Search Report and Written Opinion dated Nov. 13, 2020.
PCT/US2020/052536 filed Sep. 24, 2020 International Search Report and Written Opinion dated Dec. 4, 2020.
PCT/US2020/056364 filed Oct. 19, 2020 International Search Report and Written Opinion dated Jan. 19, 2021.
PCT/US2020/056864 filed Oct. 22, 2020 International Search Report and Written Opinion dated Jan. 14, 2021.
PCT/US2020/057202 filed Oct. 23, 2020 International Search Report and Written Opinion dated Jan. 21, 2021.
PCT/US2020/057397 filed Oct. 26, 2020 International Search Report and Written Opinion dated Mar. 10, 2021.
PCT/US2021/014700 filed Jan. 22, 2021 International Search Report and Written Opinion dated Jun. 29, 2021.
PCT/US2021/028018 filed Apr. 19, 2021 International Search Report and Written Opinion dated Sep. 13, 2021.
PCT/US2021/028683 filed Apr. 22, 2021 International Search Report and Written Opinion dated Sep. 16, 2021.
PCT/US2021/029183 filed Apr. 26, 2021 International Search Report and Written Opinion dated Sep. 24, 2021.
PCT/US2021/033443 filed May 20, 2021 International Search Report and Written Opinion dated Sep. 23, 2021.
PCT/US2021/039084 filed Jun. 25, 2021 International Search Report and Written Opinion dated Jan. 10, 2022.
PCT/US2021/039843 filed Jun. 30, 2021 International Search Report and Written Opinion dated Nov. 11, 2021.
PCT/US2021/044029 filed Jul. 30, 2021 International Search Report and Written Opinion dated Dec. 9, 2021.
U.S. Appl. No. 15/008,628, filed Jan. 28, 2016 Final Office Action dated May 30, 2018.
U.S. Appl. No. 15/008,628, filed Jan. 28, 2016 Non-Final Office Action dated Jan. 25, 2019.
U.S. Appl. No. 15/008,628, filed Jan. 28, 2016 Non-Final Office Action dated Nov. 2, 2017.
U.S. Appl. No. 15/008,628, filed Jan. 28, 2016 Notice of Allowance dated May 15, 2019.
U.S. Appl. No. 16/398,020, filed Apr. 29, 2019 Final Office Action dated Jan. 25, 2022.
U.S. Appl. No. 16/398,020, filed Apr. 29, 2019 Non-Final Office Action dated May 11, 2021.
U.S. Appl. No. 17/006,553, filed Aug. 28, 2020 Final Office Action dated Sep. 28, 2022.
U.S. Appl. No. 17/006,553, filed Aug. 28, 2020 Non-Final Office Action dated Mar. 16, 2022.
U.S. Appl. No. 17/077,728, filed Oct. 22, 2020 Non-Final Office Action dated Feb. 9, 2022.
PCT/US2023/082753 filed Dec. 6, 2023 International Search Report and Written Opinion dated May 29, 2024.
U.S. Appl. No. 17/363,500, filed Jun. 30, 2021 Non-Final Office Action dated Sep. 23, 2024.
EP 20862936.0 filed Mar. 28, 2022 Extended European Search Report dated Sep. 19, 2023.
PCT/US2023/010971 filed Jan. 17, 2023 International Search Report and Written Opinion dated Jul. 28, 2023.
U.S. Appl. No. 17/006,553, filed Aug. 28, 2020 Non-Final Office Action dated Jun. 26, 2023.

(56) References Cited

OTHER PUBLICATIONS

U.S. Appl. No. 17/006,553, filed Aug. 28, 2020 Notice of Allowance dated Sep. 11, 2023.
Yamada, T. et al., "Selective Hemi-Portocaval Shunt Based on Portal Vein Pressure for Small-for-Size Graft in Adult Living Donor Liver Transplantation." American Journal of Transplantation, Blackwell Munksgaard, DK, vol. 8, No. 4, Feb. 5, 2008 [Feb. 5, 2008] pp. 847-853.
U.S. Appl. No. 17/363,500, filed Jun. 30, 2021 Notice of Allowance dated Jan. 27, 2026.
U.S. Appl. No. 17/969,626, filed Oct. 19, 2022 Notice of Allowance dated Jan. 27, 2026.
U.S. Appl. No. 17/980,455, filed Nov. 3, 2022 Notice of Allowance dated Apr. 1, 2026.
U.S. Appl. No. 18/081,480, filed Dec. 14, 2022 Final Office Action dated Mar. 30, 2026.
U.S. Appl. No. 18/098,052, filed Jan. 17, 2023. Non-Final Office Action dated Feb. 23, 2026.
U.S. Appl. No. 18/524,480, filed Nov. 30, 2023 Non-Final Office Action dated Mar. 25, 2026.
U.S. Appl. No. 18/081,480, filed Dec. 14, 2022 Non-Final Office Action dated Jul. 23, 2026.
U.S. Appl. No. 18/098,052, filed Jan. 17, 2023 Final Office Action dated Jun. 30, 2026.

* cited by examiner

SECTION A
124
110
130

SECTION B
124
134
110
130

SECTION C
124
110
134

SECTION D
124
114
110
112
132

APPARATUS AND METHOD FOR TIPPING RAPIDLY INSERTABLE CENTRAL CATHETERS (RICC)

PRIORITY

This application claims the benefit of priority to U.S. Provisional Application No. 63/301,886, filed Jan. 21, 2022, which is incorporated by reference in its entirety into this application.

BACKGROUND

Rapidly Insertable Central Catheter ("RICC") systems include a RICC catheter having a catheter body defining two or more lumen, and an access section extending therefrom and defining a single lumen. The RICC further includes a dilator section disposed between the access section and the catheter body section and defines a tapered outer profile. The configuration of the RICC allows a clinician to perform the steps of accessing the vasculature, dilating the access site, and placing the catheter body defining one or more lumens, in a single action. Under conventional catheter placement techniques, such steps would have to be performed separately and require the repeated introduction and removal of several tools and medical devices. As such RICC systems simplify complicated and laborious placement techniques, mitigate the introduction of pathogens, and reduce the overall procedure duration.

However, forming the RICC catheter, which is required to perform several different functions, requires coupling the three different structures of the catheter body, dilator section, and access section together, while maintaining a smooth abluminal surface. Each of the three different structures are required to display different mechanical properties to fulfil the respective roles in the placement process, and as such, are often formed of different materials. Conventional manufacturing techniques results in a bump or ridge being formed adjacent a join between two or more of these structures. Where the bump occurs on an outer surface, the bump can catch a portion of the skin at the insertion site inhibiting the distal advancement of the RICC and disrupting the placement procedure. Where the bump occurs within a lumen, the bump can snag the tip of a guidewire or the like, inhibiting movement of the guidewire therethrough. Additional machining or milling procedures are required to remove such bumps or ridges and provide a smooth surface, but such secondary manufacturing procedures increase costs and complexity.

Further, conventional manufacturing techniques often require secondary machining or milling procedures to form the apertures communicating with the lumen. Either the apertures are formed in a side wall or in a distal end of the catheter, after the catheter has been formed. Forming apertures in a tapered outer surface while maintaining a smooth abluminal surface can be particularly challenging. Errors in these secondary machining procedures can lead to wastage in the manufacturing process, or failure of the device. As such apertures are often formed distally or proximally of the tapered sections and formed perpendicular to the axis of the lumen.

SUMMARY

Briefly summarized, embodiments disclosed herein are directed to distal tip structures for a catheter, such as a rapidly insertable central catheter (RICC), and associated methods of manufacture. Embodiments are directed to forming intricate distal tip structures, including one or more different materials, while improving manufacturing efficiencies. Embodiments are directed to providing a RICC distal tip structure having a smooth abluminal and intra-luminal surfaces, with little or no secondary machining procedures to remove ridges or bumps, or forming apertures. Further, embodiments are directed to forming apertures in tapered surfaces during the primary manufacturing step. Such distal tip structures reduce a longitudinal length between the apertures and a distal tip and improve the efficacy of device. Additionally, reducing the number of manufacturing steps reduces costs and wastage, and improves manufacturing efficiencies.

Disclosed herein is a method of forming a rapidly insertable central catheter including, providing a catheter body section having a primary lumen, a secondary lumen and a tertiary lumen, each extending longitudinally, placing a distal end of the catheter body within a die, the die having a first mandrel engaging the primary lumen, a second mandrel engaging the secondary lumen, and a third mandrel engaging the tertiary lumen, melting a polymeric material disposed within a cavity of the die to form a dilator section coupled to the distal tip of the catheter body, the dilator section defining a tapered out profile and including a secondary lumen aperture disposed in a side wall and communicating with the secondary lumen, and a tertiary lumen aperture disposed in a side wall and communicating with the tertiary lumen.

In some embodiments, the method further includes forming an access section integrally with the dilator section and extending from a distal end thereof, the access section defining a single lumen communicating with primary lumen and extending to a primary lumen aperture disposed at a distal tip thereof.

In some embodiments, wherein the access section and the dilator section are formed of a first polymeric material and the catheter body is formed of a second polymeric material, the first polymeric material displaying a harder durometer relative to the second polymeric material.

In some embodiments, wherein the first mandrel includes a collar disposed at a distal end thereof, the collar defining an outer diameter equal to an outer diameter of an access section.

In some embodiments, the method further includes placing a proximal end of the access section within a receptacle of the dilator section, defined by the collar of the first mandrel and securing the access section to the dilator section using adhesive, bonding, solvent bonding, or welding.

In some embodiments, the access section is formed of a first polymeric material and the catheter body is formed of a second polymeric material, the first polymeric material displaying a harder durometer relative to the second polymeric material.

In some embodiments, the dilator section is formed of one of the first polymeric material, the second polymeric material, or a third polymeric material having a harder durometer relative to the second polymeric material and a softer durometer relative to the first polymeric material.

In some embodiments, the melting step further includes applying one of radio frequency (RF) energy or thermal energy to melt the polymeric material.

In some embodiments, one or both of the secondary lumen aperture and the tertiary lumen aperture are disposed in a longitudinal mid-point of the dilator section between a proximal end and a distal end.

In some embodiments, the secondary lumen aperture and the tertiary lumen aperture are disposed at an equal longitudinal length relative to a distal tip of the rapidly insertable central catheter.

In some embodiments, the method further includes forming an introducing aperture disposed proximally of one or both of the secondary lumen aperture and the tertiary lumen aperture and communicating with the primary lumen, the introducing aperture configured to receive an access needle therethrough, a distal tip of the access needle extending through a primal lumen aperture disposed at a distal tip of the rapidly insertable central catheter.

In some embodiments, providing a catheter body further includes extruding or trimming the catheter body section to a predetermined length and coupling a proximal end of the catheter body to one or more of a catheter hub and one or more extension legs.

Also disclosed is a rapidly insertable central catheter system including, a rapidly insertable central catheter having, a catheter body defining a primary lumen, a secondary lumen, and a tertiary lumen, and including an introducing aperture disposed in a side wall and communicating with the primary lumen, a dilator section extending distally from the catheter body and defining a tapered outer profile, the dilator section defining a secondary lumen aperture disposed in a side wall and communicating with the secondary lumen and defining a tertiary lumen aperture disposed in a side wall and communicating with the tertiary lumen, and an access section extending from the dilator section and including a primary lumen aperture disposed at a distal tip thereof and communicating with the primary lumen, and a needle extending through the introducing aperture and through a distal portion of the primary lumen, a distal tip of the needle extending through the primary lumen aperture.

In some embodiments, the secondary lumen aperture and the tertiary lumen aperture are disposed at an equal longitudinal length from a distal tip of the access section.

In some embodiments, a longitudinal length of the access section is less than a longitudinal length of the dilator section.

In some embodiments, the access section is formed of a first material and the catheter body is formed of a second material having a softer durometer relative to the first material.

In some embodiments, the dilator section is formed of one of the first material, the second material or a third material having a harder durometer relative to the second material and a softer durometer relative to the first material.

In some embodiments, the dilator section and the access section are formed integrally as a single monolithic piece and fused with the catheter body using RF welding.

In some embodiments, the dilator section is fused with the catheter body using RF welding and defines a receptacle at a distal end, the receptacle having a diameter equal to an outer diameter of the access section, a proximal end of the access section coupled with the receptacle using adhesive, bonding, solvent bonding, or welding.

These and other features of the concepts provided herein will become more apparent to those of skill in the art in view of the accompanying drawings and following description, which describe particular embodiments of such concepts in greater detail.

DRAWINGS

DESCRIPTION

Figure 1:
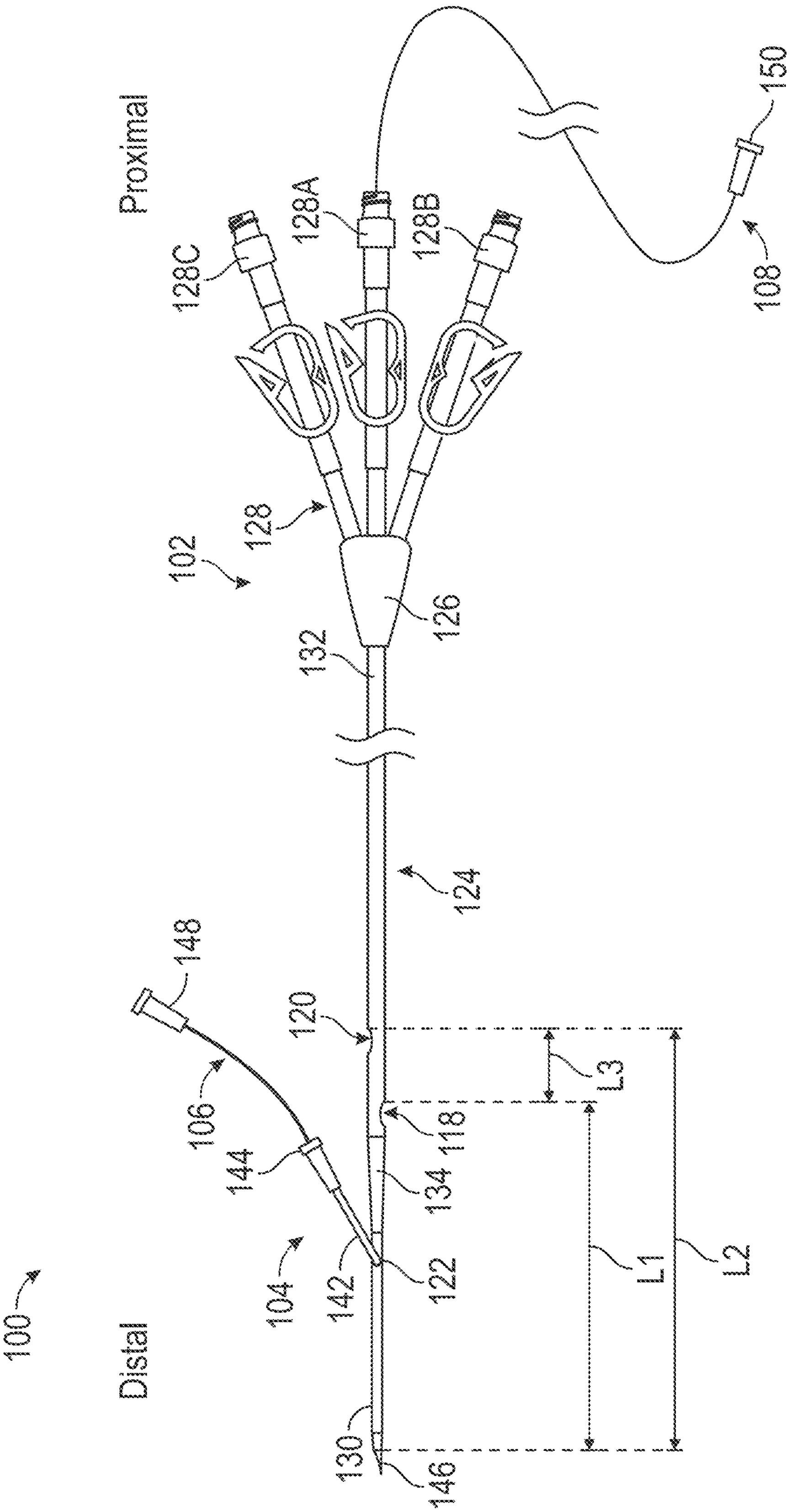
FIG. 1 shows a side view of an exemplary RICC placement system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Figure 4A:
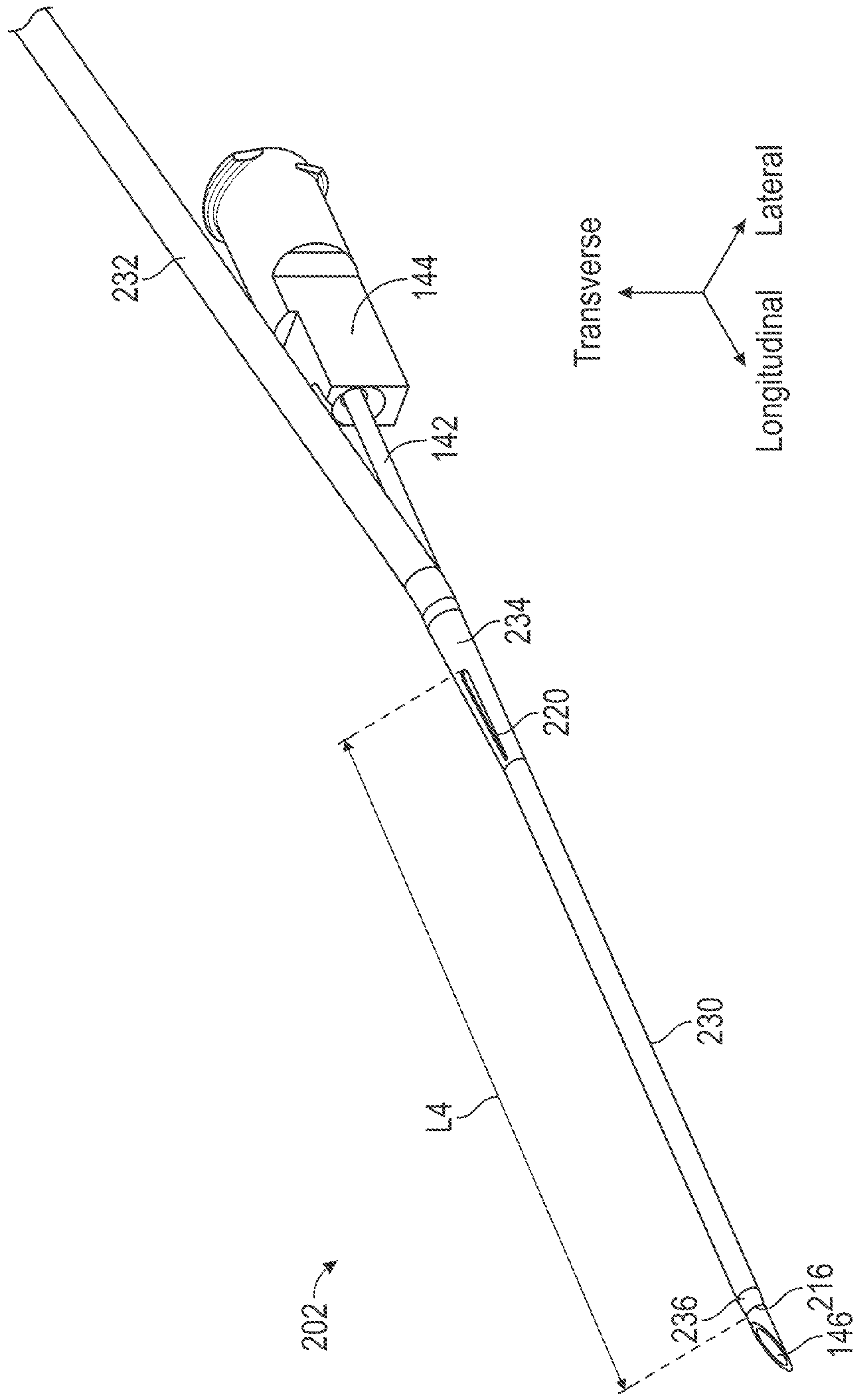
FIG. 4A shows a perspective view of a RICC placement system, in accordance with embodiments disclosed herein.

To assist in the description of embodiments described herein, as shown in FIG. 4A, a longitudinal axis extends substantially parallel to an axial length of the catheter. A lateral axis extends normal to the longitudinal axis, and a transverse axis extends normal to both the longitudinal and lateral axes. A horizontal plane is defined by the longitudinal and lateral axes. A vertical plane extends normal to the horizontal plane.

Unless defined otherwise, all technical and scientific terms used herein have the same meaning as commonly understood by those of ordinary skill in the art.

As discussed herein, there is a need to overcome certain artifacts in the manufacturing of rapidly insertable central catheters (RICC). For example, a RICC can include a multiluminal, catheter body section, and can transition to a monoluminal access section adjacent a distal end thereof. The transition between these sections can be considerably difficult to manufacture without creating an edge or bump on an outer surface of the RICC that catches the skin of a patient around an insertion site and obstructs placement of the RICC subcutaneously. Therefore, also disclosed herein are RICCs and methods of manufacture thereof that address the foregoing need.

Rapidly Insertable Central Catheter Systems

FIGS. 1-3D illustrate an exemplary rapidly insertable central catheter ("RICC") placement system ("system") 100 in accordance with some embodiments. As shown, the system 100 generally includes a rapidly insertable central catheter ("RICC") 102, an introducer needle ("needle") 104, and one or more guidewires, for example, an access guidewire 106, and a placement guidewire 108.

Figures 3A, 3B, 3C, 3D:
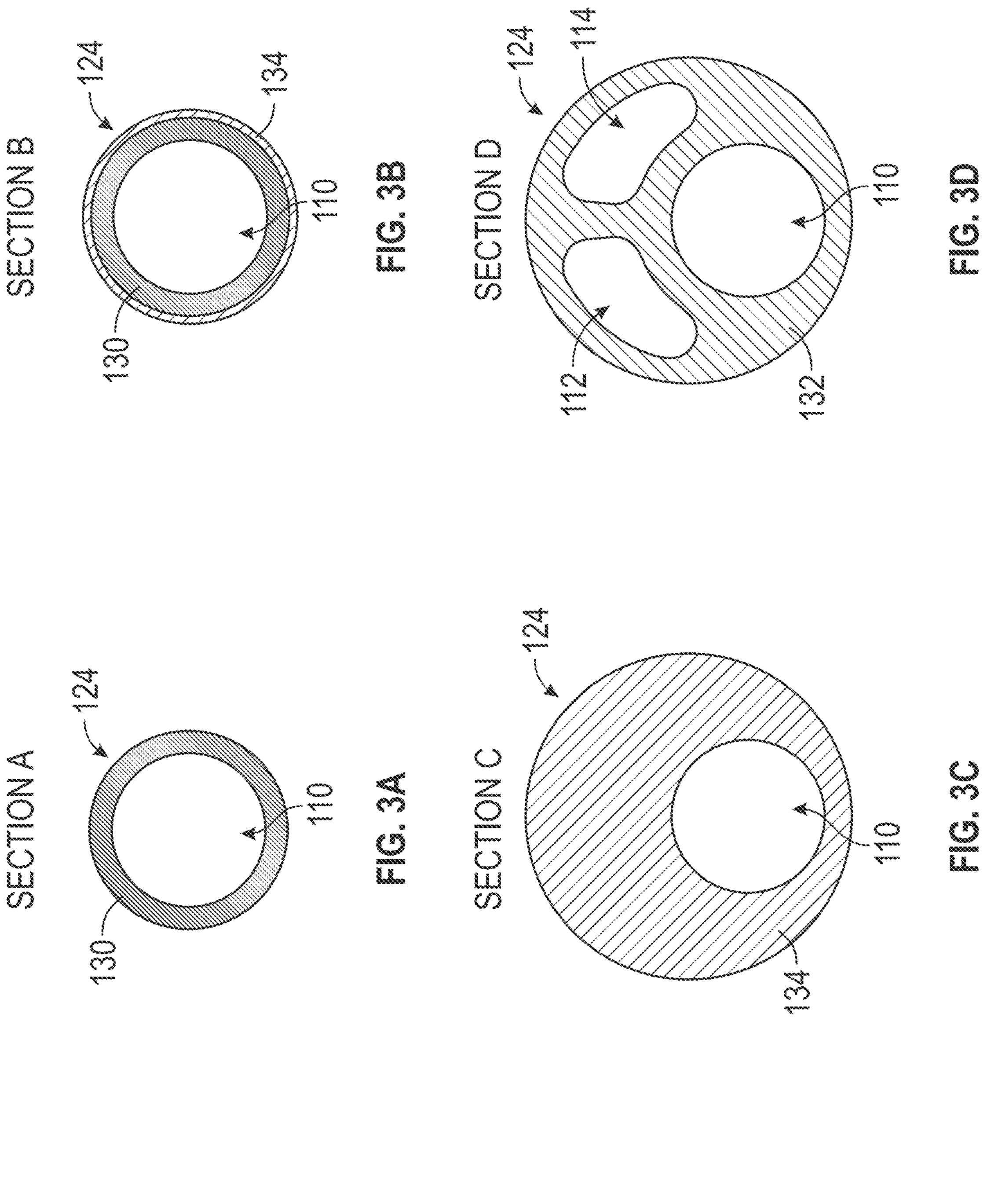
FIGS. 3A-3D show various cross-sectional views of the distal portion of FIG. 2, in accordance with embodiments disclosed herein.

In an embodiment, the RICC 102 can be a monoluminal or multiluminal RICC (e.g., a diluminal RICC, a triluminal RICC, a tetraluminal RICC, a pentaluminal RICC, a hexaluminal RICC, etc.). As shown in FIGS. 1 and 3D, the RICC 102 is a triluminal RICC including a set of three lumens. Such a set of three lumens includes a primary lumen 110 (e.g., a distal lumen), a secondary lumen 112 (e.g., a medial lumen), and a tertiary lumen 114 (e.g., a proximal lumen).

As shown in FIG. 1, the RICC 102 further includes a hub 126 disposed at a proximal end, and one or more extension legs 128 extending proximally from the hub 126. Each extension leg 128 is in fluid communication with a lumen 110, 112, or 114 of the RICC 102. For example, as shown, a first extension leg 128A is in fluid communication with the distal lumen 110, a second extension leg 128B is in fluid communication with the medial lumen 112, and a third extension leg 128C is in fluid communication with the proximal lumen 114.

Whether the RICC 102 is monoluminal or multiluminal, the RICC 102 includes at least the primary lumen 110. The primary lumen 110 typically extends from a proximal end of the RICC 102 to a distal end of the RICC 102 such as from an opening of a corresponding Luer connector to a primary-lumen aperture 116 in a distal end of the catheter tube 124 (e.g., the hard portion of the catheter tube 124 or the first section (access section 130) of the catheter tube 124) set forth herein. When the RICC 102 has two or more lumens, the RICC 102 further includes at least the secondary lumen 112. The secondary lumen 112 typically extends from the proximal end of the RICC 102 to a distal portion of the RICC 102 such as from an opening of a corresponding Luer connector to a secondary-lumen aperture 118 in the distal portion of the catheter tube 124 (e.g., the soft portion of the catheter tube 124 or the second section (catheter body 132) of the catheter tube 124) proximal of the primary-lumen aperture 116.

When the RICC 102 has three or more lumens, the RICC 102 further includes at least the tertiary lumen 114. The tertiary lumen 114 typically extends from the proximal end of the RICC 102 to the distal portion of the RICC 102 such as from an opening of a corresponding Luer connector to a tertiary-lumen aperture 120 in the distal portion of the catheter tube 124 (e.g., the soft portion of the catheter tube 124 or the first section 132 of the catheter tube 124) proximal of the secondary-lumen aperture 118. Notwithstanding the foregoing, each lumen of the secondary lumen 112 and the tertiary lumen 114 can distally extend slightly farther than the secondary-lumen aperture 118 and the tertiary-lumen aperture 120, respectively, in view of different manufacturing methods.

In an embodiment, a longitudinal length between a primary-lumen aperture 116 and a secondary-lumen aperture 118 can be a first length (L1). In an embodiment, a longitudinal length between a primary-lumen aperture 116 and a tertiary-lumen aperture 120 can be a second length (L2). In an embodiment, the first length (L1) can be greater than the second length (L2). As such a difference between the first length (L1) and the second length (L2) can be a third length (L3). In an embodiment, the first length (L1) or the second length (L2) can be between 3 cm and 10 cm. In an embodiment, the first length (L1) or the second length (L2) can be substantially 7 cm. However it will be appreciated that greater or lesser lengths are also contemplated.

In an embodiment, the RICC 102 includes an introducing aperture 122, which is dedicated to accommodating insertion of the introducer needle 104 therethrough for coupling the RICC 102 and the introducer needle 104 together in the system 100. However, the RICC 102 need not include a dedicated introducing aperture such as the introducing aperture 122. Indeed, the secondary-lumen aperture 118 or the tertiary-lumen aperture 120 can serve as the introducing aperture 122 in some embodiments, which requires a different mode of coupling the RICC 102 and the introducer needle 104. Alternatively, such as when the RICC 102 is monoluminal, an introducing aperture can be created as needed by puncturing the catheter tube 124 with the introducer needle 104.

The RICC 102 further includes an introducing lumen coincident with a distal portion of the primary lumen 110. In other words, the introducing lumen is an introducing portion of the primary lumen 110 of the RICC 102. In the RICC 102, the introducing lumen is the distal portion of the primary lumen 110 extending from the introducing aperture 122 to the primary-lumen aperture 116. The introducing aperture 122, which can be distal of the secondary-lumen aperture 118, between the secondary-lumen aperture 118 and the tertiary-lumen aperture 120, or proximal of the tertiary-lumen aperture 120, opens directly into a proximal end of the introducing portion of the primary lumen 110 of the RICC 102. For a RICC without the introducing aperture 122, the introducing lumen is the distal portion of the primary lumen 110 extending from the secondary-lumen aperture 118, the tertiary-lumen aperture 120, or a puncture created with the introducer needle 104 to the primary-lumen aperture 116. Whether the introducing lumen extends from the secondary-lumen aperture 118, the tertiary-lumen aperture 120, or the puncture depends upon which aperture of the foregoing apertures accommodates the introducer needle 104. Neither the secondary-lumen aperture 118 nor the tertiary-lumen aperture 120 opens directly into a proximal end of the introducing portion of the primary lumen 110 of the RICC without the introducing aperture 122. Instead, the introducer needle 104 pierces a septum between the secondary lumen 112 or the tertiary lumen 114 and the primary lumen 110 respectively by way of the secondary-lumen aperture 118 or the tertiary-lumen aperture 120.

Figure 2:
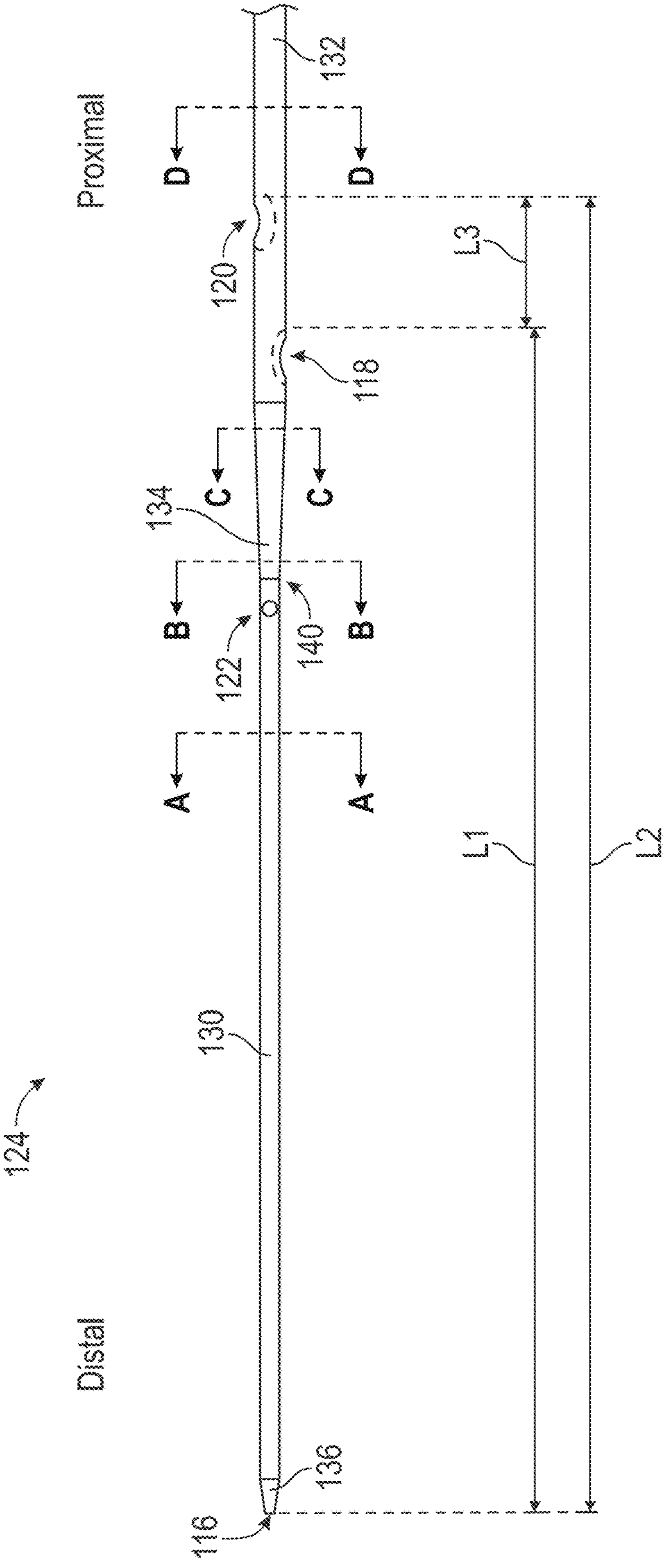
FIG. 2 shows close up detail of a distal portion of the RICC of FIG. 1, in accordance with embodiments disclosed herein.

FIG. 2 illustrates a distal portion of the catheter tube 124 of the RICC 102 of FIG. 1 in accordance with some embodiments. FIGS. 3A-3D illustrate various transverse cross sections of the catheter tube 124 of FIG. 2 in accordance with some embodiments.

The catheter tube 124 includes a hard portion of the catheter tube 124 and a soft portion of the catheter tube 124, wherein "hard" and "soft" are used in a relative sense in that the hard portion of the catheter tube 124 is harder than the soft portion of the catheter tube 124. The hard potion of the catheter tube 124 includes a first, monoluminal section, or "access section" 130 in a distal portion of the catheter tube 124, and the soft potion of the catheter tube 124 includes a second section, or "catheter body" 132 having one or more lumens and extending from a proximal portion of the catheter tube 124 to the distal portion thereof but proximal of the access section 130. In an embodiment, a dilation section 134, or dilator section 134 of the catheter tube 124 can be formed of the same material as the access section 130 and can display the same mechanical properties thereof. In an embodiment, the dilator section 134 of the catheter tube 124 can be formed of the same material as the catheter body section 132 and can display the same mechanical properties thereof. In an embodiment, the dilator section 134 of the catheter tube 124 can be formed of a third material different from that of the first material of the access section 130 and the second material of the catheter body section 132. In an embodiment, the third material can be softer than the relatively hard first material and harder than the relatively soft second material. In an embodiment, the third material can be softer than the second material of the catheter body section 132. In an embodiment, the third material can be harder than the first material of the access section 130.

In an embodiment, the foregoing arrangement of the access section 130 of the catheter tube 124, the catheter body section 132 of the catheter tube 124, and the dilator section 134 possess a column strength sufficient to prevent buckling of the catheter tube 124 when inserted into an insertion site established by a percutaneous puncture and advanced through a vasculature of a patient. As set forth herein, the catheter tube 124 is shown with the introducing aperture 122 through a side of the catheter tube 124 in a distal portion thereof, e.g. an access section 130.

The access section 130 of the catheter tube 124 is in the distal portion of the catheter tube 124. The access section 130 includes a distal tip 136 having a relatively short taper continuing from the beveled tip 146 of the introducer needle 104 in the system 100 to an outer diameter of a remainder of the access section 130. The taper of the distal tip 136 is configured for immediate dilation of tissue about a percutaneous puncture established with the introducer needle 104 up to the outer diameter of the remainder of the access section 130 of the catheter tube 124. The access section 130 also includes a proximal portion disposed in the receptacle 138 of the dilator section 134 and fixedly coupled (e.g., solvent bonded, adhered, welded, etc.) thereto.

The access section 130 of the catheter tube 124 is formed of a first polymeric material having a first durometer. The first polymeric material can be polytetrafluoroethylene, polypropylene, or polyurethane, but the first polymeric material is not limited to the foregoing polymers. Polyurethane is advantageous in that the access section 130 of the catheter tube 124 can be relatively rigid at room-temperature but become more flexible in vivo at body temperature, which reduces irritation to vessel walls and phlebitis.

The catheter body section 132 of the catheter tube 124 extends from the proximal portion of the catheter tube 124 to the distal portion thereof but proximal of the access section 130 of the catheter tube 124. In an embodiment, the catheter body section 132 includes a distal end integral (e.g., RF welded) with a proximal end of the dilator section 134 and a proximal portion disposed in the catheter hub 126 and fixedly coupled (e.g., solvent bonded, welded, adhered, etc.) thereto.

The catheter body section 132 of the catheter tube 124 is formed of a second polymeric material having a second durometer less than the first durometer. The second polymeric material can be polyvinyl chloride, polyethylene, polyurethane, or silicone, but the second polymeric material is not limited to the foregoing polymers. In addition to that set forth above for polyurethane in the access section 130 of the catheter tube 124, polyurethane is advantageous in that it can be less thrombogenic than some other polymers.

The dilator section 134 of the catheter tube 124 couples the access section 130 and the catheter body section 132 of the catheter tube 124 together. The dilator section 134 includes a receptacle 138 (see FIG. 8D) in a distal portion including the proximal portion of the access section 130 of the catheter tube 124 disposed therein and fixedly coupled (e.g., solvent bonded, welded, adhered, etc.) thereto. The proximal end of the dilator section 134 is integral (e.g., RF welded) with the distal end of the catheter body section 132 of the catheter tube 124, which, in an embodiment effectively terminates the lumens (e.g. the medial and proximal lumens 112, 114), of the catheter body section 132 of the catheter tube 124 other than the primary lumen 110 from passing through the dilator section 134.

In an embodiment, the dilator section 134 also includes a taper over its length from a distal end to the proximal end configured for immediate dilation of tissue about the percutaneous puncture, up to an outer diameter of the catheter body section 132 of the catheter tube 124. An abluminal surface of the dilator section 134 smoothly transitions from an abluminal surface of the proximal portion of the access section 130 without an edge that catches on skin when the RICC 102 is inserted into an insertion site of a patient. In addition to the edge being minimal to negligible, the edge can include solvent-interdiffused polymeric material of the first polymeric material and the polymeric material of the dilator section 134, which smoothens the transition from the access section 130 of the catheter tube 124 to the dilator section 134.

In an embodiment, the dilator section 134 of the catheter tube 124 is formed of the second polymeric material or a third polymeric material having a third durometer closer to the second durometer than the first durometer. Again, the second polymeric material can be polyvinyl chloride, polyethylene, polyurethane, or silicone, but the second polymeric material is not limited to the foregoing polymers.

Again, the access section 130 of the catheter tube 124 is formed of a first polymeric material having a first durometer, the catheter body section 132 of the catheter tube 124 is formed of a second polymeric material having a second durometer less than the first durometer, and the dilator section 134 of the catheter tube 124 is formed of the second polymeric material or a third polymeric material having a third durometer closer to the second durometer than the first durometer. Being that each durometer of the second durometer and the third durometer is less than the first durometer, the soft portion of the catheter tube 124 including the second portion of the catheter tube 124 and the dilator section 134 is softer than the hard portion of the catheter tube 124 including the access section of the catheter tube 124. In other words, the first durometer is greater than each durometer of the second durometer and the third durometer. Being that the first durometer is greater than each durometer of the second durometer and the third durometer, the hard portion of the catheter tube 124 including the access section of the catheter tube 124 is harder than the soft portion of the catheter tube 124 including the second portion of the catheter tube 124 and the dilator section 134.

It should be understood the first durometer of the first polymeric material, the second durometer of the second polymeric material, and the third durometer of the third polymeric material can be on different scales (e.g., Type A or Type D), so the second durometer or the third durometer might not be numerically less than the first durometer. In other words, the first durometer material might not be numerically greater than the second durometer or the third durometer in view of the different scales. That said, the hardness of the second or third polymeric material can still be less than the hardness of the first polymeric material or the hardness of the first polymeric material can still be greater than the hardness of the second or third polymeric material because the different scales—each of which ranges from 0 to 100—are designed for characterizing different materials in groups of the materials having a like hardness.

Notwithstanding the foregoing, the access section 130 of the catheter tube 124, the catheter body section 132 of the catheter tube 124, and the dilator section 134 can be formed of a same polymeric material or different polymeric materials having substantially equal durometers provided the column strength of the catheter tube 124 is sufficient to prevent buckling of the catheter tube 124 when inserted into an insertion site established by a percutaneous puncture and advanced through a vasculature of a patient.

In an embodiment, each extension leg of the one-or-more extension legs 128 typically includes a Luer connector coupled to the extension leg, through which Luer connector, the extension leg, and the extension-leg lumen thereof can be connected to another medical device. In an embodiment, the introducer needle 104 includes a shaft 142, a needle hub 144 about a proximal portion of the shaft 142, and a beveled tip 146 in a distal portion of the shaft 142.

When the system 100 is in the ready-to-deploy state, the introducer needle 104 or the shaft 142 thereof is disposed in the introducing lumen through the introducing aperture 122 (if present), such that the beveled tip 146 of the introducer needle 104 extends past the distal end of the access section 130 of the catheter tube 124 for establishing a percutaneous puncture. The access guidewire 106 includes a length sufficient for advancing the access guidewire 106 a sufficient distance into a blood-vessel lumen upon establishing access thereto for advancing the distal portion of the RICC 102 into the blood-vessel lumen for maintaining access.

The access guidewire 106 is disposed in a needle lumen of the introducer needle 104 when the system 100 is in at least the ready-to-deploy state. Indeed, a distal end of the access guidewire 106 is proximal of the beveled tip 146 of the introducer needle 104 but distal of the dilator section 134, which allows for immediate advancement of the distal end of the access guidewire 106 beyond the beveled tip 146 of the introducer needle 104 and into a blood-vessel lumen upon establishing access thereto.

The access guidewire 106 includes a stop 148 (e.g., a hub, a ball, a slug, etc.) about a proximal portion of the access guidewire 106 forming a stop end (e.g., a hub end, a ball end, a slug end, etc.) of the access guidewire 106. The stop end of the access guidewire 106 is larger than any aperture of the RICC 102 or the catheter tube 124 thereof, thereby providing a distal limit for advancing the access guidewire 106 into the RICC 102. The placement guidewire 108 includes an atraumatic tip (e.g., a coiled or partially coiled tip) and a length sufficient for advancing the placement guidewire 108 to the lower ⅓ of the superior vena cava ("SVC") of the heart.

When the system 100 is in at least the ready-to-deploy state, the placement guidewire 108 is disposed in the primary lumen 110 of the RICC 102 such that a distal end of the placement guidewire 108 is proximal of the introducing aperture 122 but distal of the catheter hub 126, which allows for immediate advancement of the distal end of the placement guidewire 108 into the blood-vessel lumen upon removing the introducer needle 104 or the shaft 142 thereof from the introducing lumen. Indeed, the placement guidewire 108 cannot be distally advanced into the introducing lumen due the presence of the introducer needle 104 or the shaft 142 thereof in at least the ready-to-deploy state of the system 100.

The placement guidewire 108 includes a stop 150 (e.g., a hub, a ball, a slug, etc.) about a proximal portion of the placement guidewire 108 forming a stop end (e.g., a hub end, a ball end, a slug end, etc.) of the placement guidewire 108. The stop end of the placement guidewire 108 is larger than a proximal end opening in the Luer connector of the extension leg in which the placement guidewire 108 is disposed, thereby providing a distal limit for advancing the placement guidewire 108 into the RICC 102.

Figure 4B:
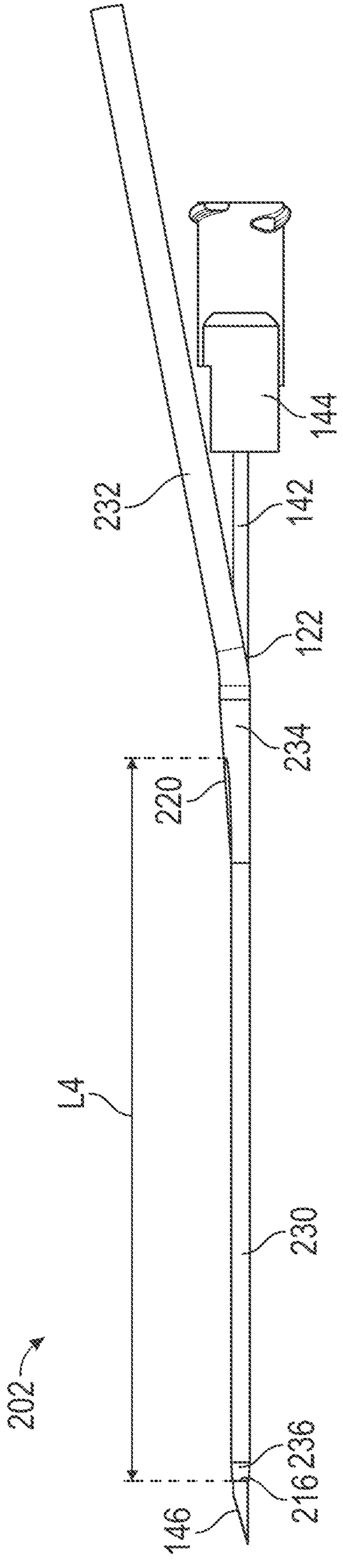
FIG. 4B shows a side view of the RICC placement system of FIG. 4A, in accordance with embodiments disclosed herein.
Figure 5:
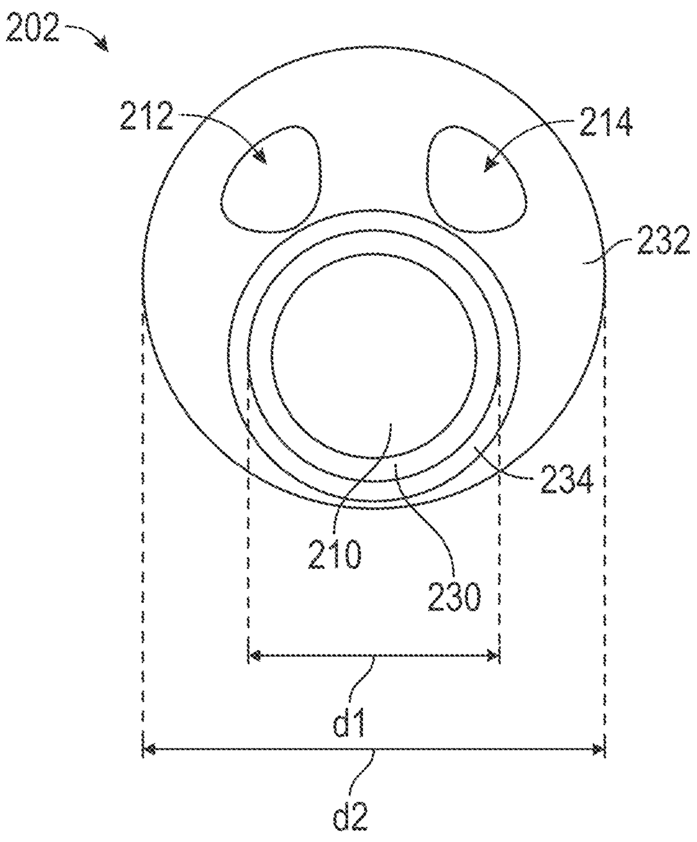
FIG. 5 shows a distal end view of the RICC of the RICC placement system of FIG. 4A, in accordance with embodiments disclosed herein.

FIGS. 4A-4B show an embodiment of a RICC 202 configured to use with a RICC system 100 as described herein. The RICC 202 generally includes a monoluminal access section 230 disposed distally and defining a first diameter (d1), and a multiluminal catheter body section 232 disposed proximally and defining a second diameter (d2). The first diameter (d1) can be less than the second diameter (d2). The RICC 202 further includes a dilator section 234 disposed between the access section 230 and the catheter body section 232 and can define a tapered abluminal surface extending between the first diameter (d1) and the second diameter (d2), as described herein. In an embodiment, one or more of the medial or secondary lumen aperture 218, and the proximal or tertiary lumen aperture 220 are formed within the tapered dilator section 134. In an embodiment, the secondary lumen aperture 218 and the tertiary lumen aperture 220 are disposed at an equal longitudinal length (L4) from the primary lumen aperture 216. In an embodiment, the length (L4), is between 0.1 cm and 7 cm. However, it will be appreciated that greater or lesser distances are also contemplated. In an embodiment, an introducing aperture 122 is disposed proximally of the dilator section 234, i.e. proximally of the secondary lumen aperture 218 and the tertiary lumen aperture 220 and communicates with the primary lumen 210.

Figure 6A:
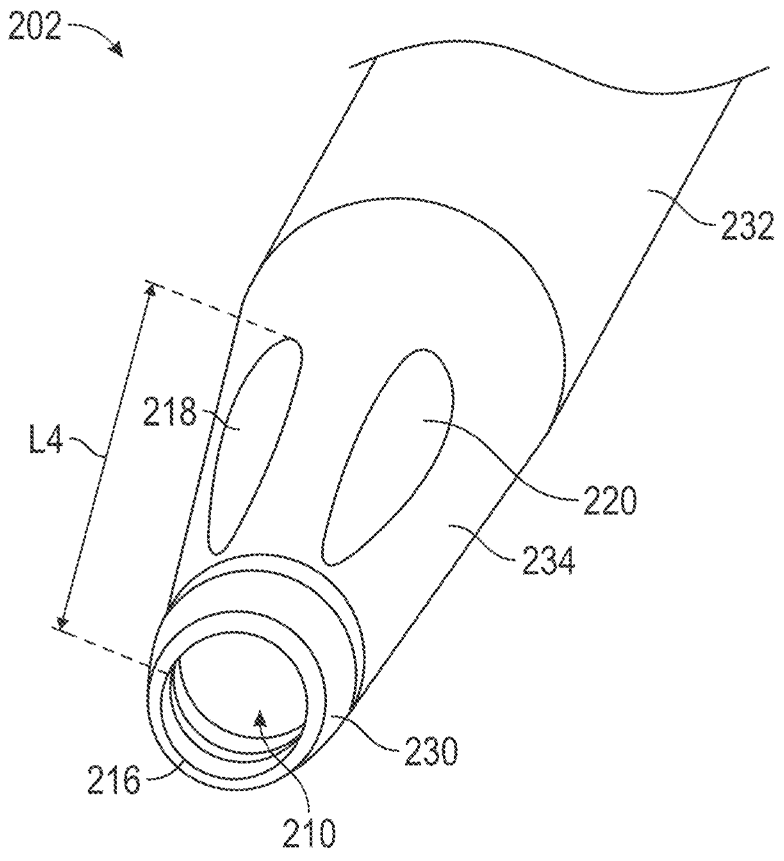
FIG. 6A shows a perspective view of a distal portion of a RICC, in accordance with embodiments disclosed herein.
Figure 6B:
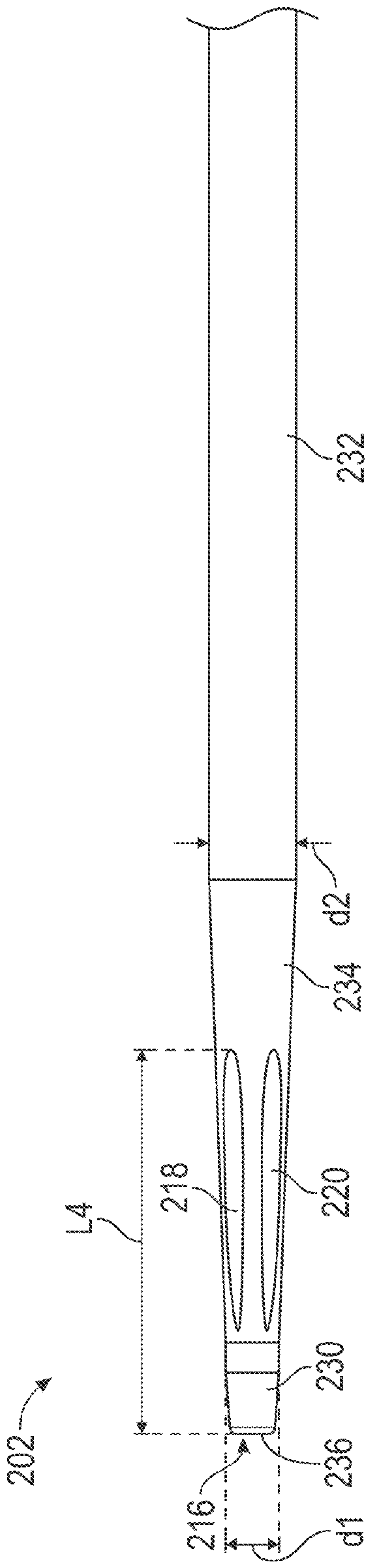
FIG. 6B shows a plan view of a distal portion of a RICC, in accordance with embodiments disclosed herein.
Figure 6C:
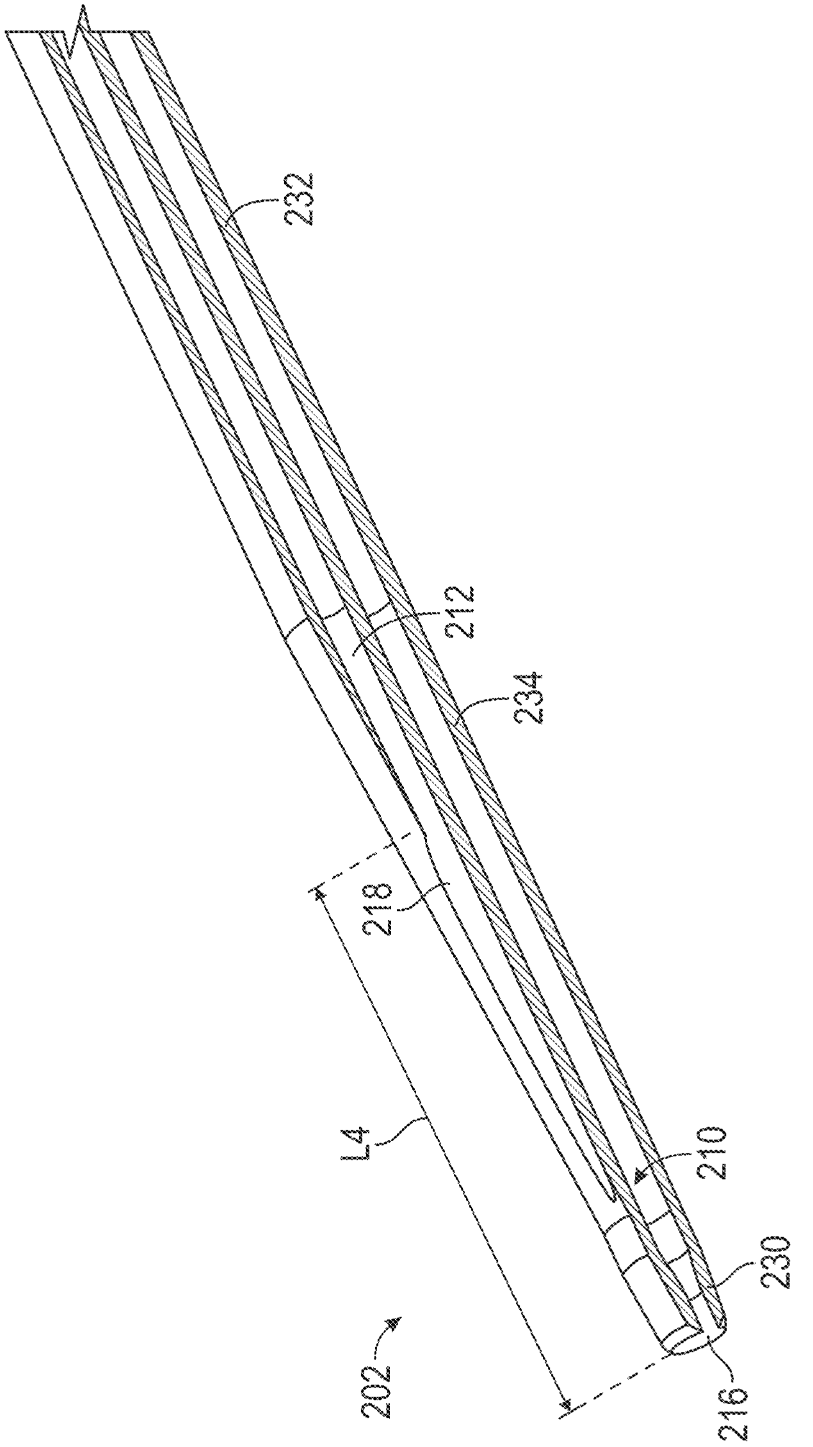
FIG. 6C shows longitudinal cross-section view of a RICC, in accordance with embodiments disclosed herein.

Advantageously, as shown in FIGS. 6A-6C, with the secondary lumen aperture 218 and the tertiary lumen aperture 220 disposed in the tapered dilator section 234, and the introducing aperture 122 disposed proximally of the dilator section 234, the longitudinal length of the access section 230 can be shortened to reduce the distance (L4) between the primary lumen aperture 216 and one or both of the secondary lumen aperture 218 and the tertiary lumen aperture 230. This can reduce the distance between an introduction site of a first fluid introduced at the primary lumen aperture 216, and a second or third fluid introduced at the secondary lumen aperture 218 or the tertiary lumen aperture 220, respectively. The positioning of the distal tip of the RICC catheter 202 within the vasculature can be critical. Where a fluid is introduced at an aperture, e.g. the secondary lumen aperture 218 or the tertiary lumen aperture 220, which is placed proximally of the target location within the vasculature, the effectiveness of the treatment is reduced. Similarly, where a distal tip 236 of the catheter 202, substantially at the primary lumen aperture 216, is advanced too far, (i.e. distally of the target location) the distal tip 236 can cause complications to the patient. For example, the distal tip 236 can be advanced into an atrium of the heart causing arrhythmia. As such, a reduced longitudinal distance between the primary lumen aperture 216 and one or both of the secondary lumen aperture 218 and the tertiary lumen aperture 220 can increase the accuracy of placement of the fluids at a target location within the vasculature.

Figure 7C:
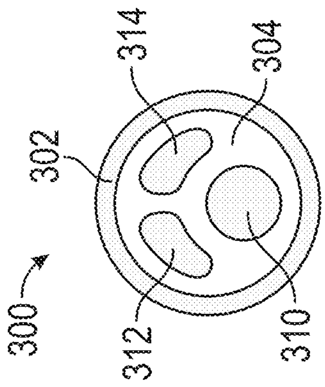
FIG. 7C shows a lateral cross-section view of the die of FIG. 7A, in accordance with embodiments disclosed herein.
Figure 7A:
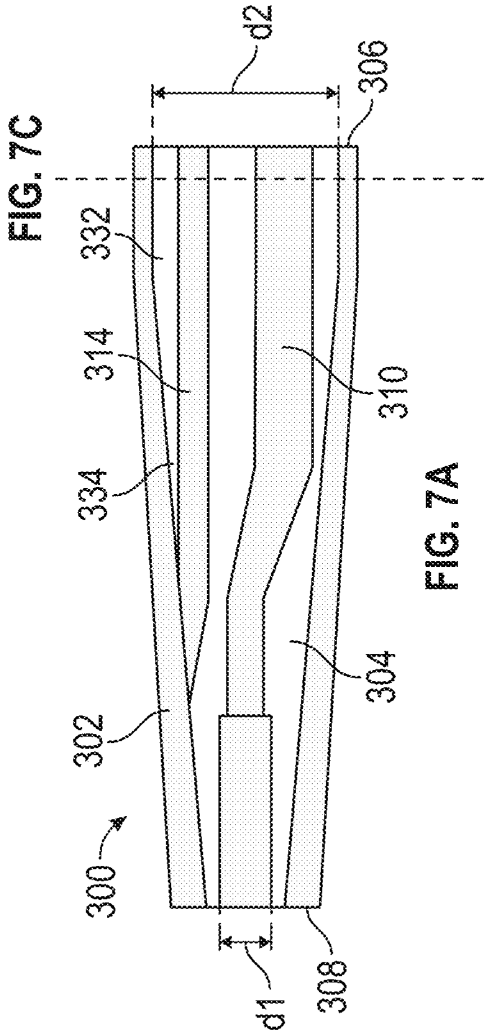
FIG. 7A shows a longitudinal vertical cross-section view of a die, in accordance with embodiments disclosed herein.
Figure 7B:
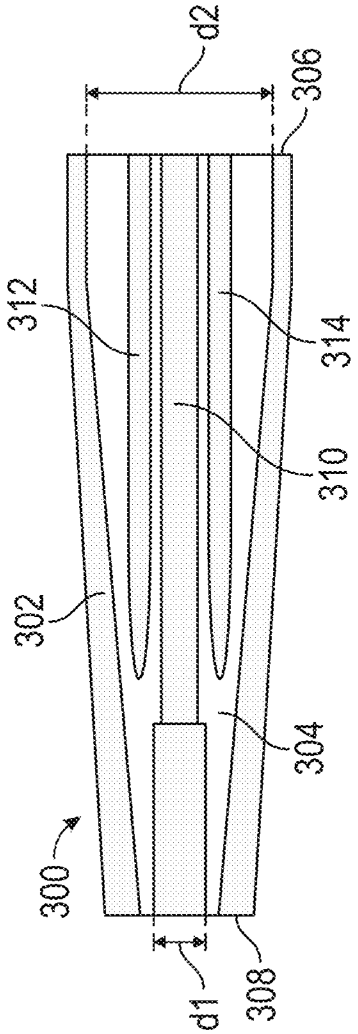
FIG. 7B shows a longitudinal horizontal cross-section view of the die of FIG. 7A, in accordance with embodiments disclosed herein.

FIGS. 7A-7C show details of a die 300 used in a manufacturing process to form at least a portion of the RICC catheter 202, as described herein. The die 300 generally includes a body 302 defining a cavity 304 that extends between a proximal end 306 of the body 302 and a distal end 308 of the body 302. In an embodiment, an interior surface of the cavity 304 defines a shape that matches an abluminal surface of a portion of the RICC 202, for example a portion of the access section 230, the catheter body section 232, the dilator section 234, or combinations thereof. For example, the cavity 304 includes a tapered cavity 334 defining a tapered inner profile. In an embodiment, the tapered cavity 334 extends between the first diameter (d1) and the second diameter (d2). As such, the tapered inner profile of the tapered cavity 334 matches the tapered outer profile of a dilator section 234 of the RICC 202.

In an embodiment, the cavity 304 further includes a catheter section 332 defining a cylindrical inner profile. An inner diameter of the catheter section 332 can match the outer diameter of a catheter body 232 of the RICC 202, i.e. the second diameter (d2). In an embodiment, the cavity 304 further includes an access section cavity (not shown) defining a cylindrical inner profile. An inner diameter of the access section cavity matches the outer diameter of the access section 230 of the RICC 202, i.e. the first diameter (d1).

In an embodiment, the die 300 further includes one or more mandrels extending substantially longitudinally through cavity 304 and shaped to define a profile of a portion of one or more lumens 210, 212, 214, as described in more detail herein. For example, the die 300 includes a primary mandrel 310 extending between a proximal end 306 and a distal end 308 thereof and configured to define a portion of the primary lumen 310. The die 300 further includes one of a secondary mandrel 312 and a tertiary mandrel 314 extending from an inner surface of the cavity 304 and extending to a proximal end 306 of the body 302 and configured to define a portion of one of a secondary lumen 212 and a tertiary lumen 214, respectively. In an embodiment, one of a secondary mandrel 312 and a tertiary mandrel 314 extends from a wall of the tapered cavity 334 of the cavity 304. In an embodiment, the secondary mandrel 312 and the tertiary mandrel 314 is configured to form one of the secondary lumen aperture 218 and the tertiary lumen aperture 220, as described in more detail herein.

Methods

FIGS. 8A-8F show an exemplary method of forming a catheter tip for a RICC 202, termed "tipping." Advantageously, the tipping process can form a portion of distal end of the RICC 202, including one or more of the access section 230, the catheter body 232, the dilator section 234, or combinations thereof, formed of one or more of the first material, second material, or third material, or combinations thereof, as described herein. Each of the access section 230, the catheter body 232, and the dilator section 234 can display different mechanical properties and perform different functions in the placement procedure and can maintain a smooth abluminal surface therebetween. Further, embodiments described herein provide a smooth transition between inner surfaces of one or more lumen 210, 212, 214. This eliminates difficulties with guidewires catching between luminal surfaces of the access section 230, the dilator section 134, and the catheter body section 232.

Figure 8A:
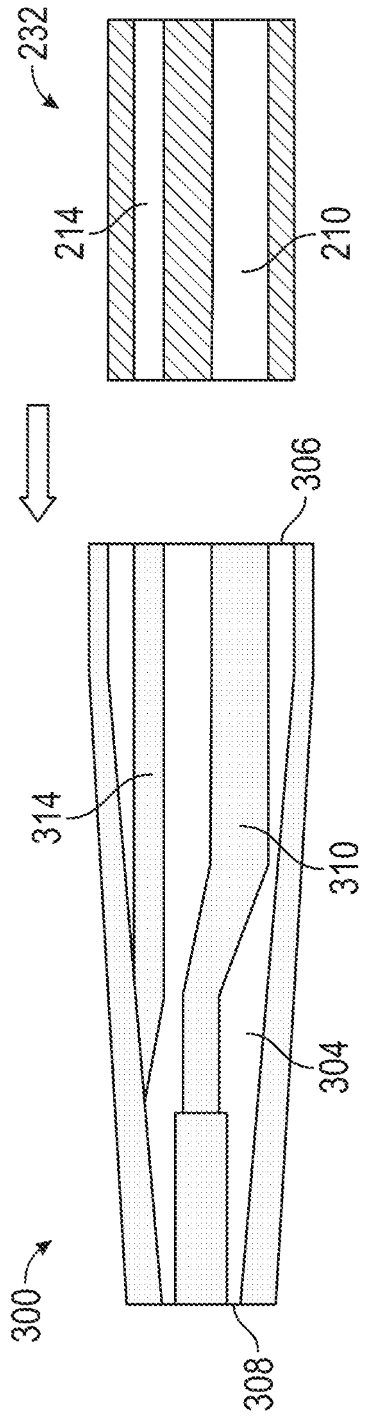
FIGS. 8A-8F show an exemplary method of forming a catheter tip, in accordance with embodiments disclosed herein.

As shown in FIG. 8A, initially a catheter body section 232 can be provided by obtaining or forming the catheter body section 232 of the RICC 202. The catheter body section 232 can be formed of the second polymeric material having the second durometer. The catheter body section 232 can be formed, for example, by extruding the catheter body section 232, and cutting the catheter body section 232 to an appropriate length. The catheter body section 232 can be monoluminal or multiluminal with one or more additional lumens to the primary lumen 210.

FIG. 8A also shows a die 300 including the one or more mandrels 310, 312, 314, as described herein. A distal end of the catheter body section 232 is inserted longitudinally into a proximal end of the cavity 304. More specifically, the distal end of the catheter body section 232 is received within the catheter section 332 of the cavity 304. An inner diameter of the catheter section 332 of the cavity 304 is equal to, or slightly smaller than, an outer diameter of the distal end of the catheter body section 232 to engage the catheter body section 232 in an interference fit.

In an embodiment, one or more of the mandrels 310, 312, 314, extends to a proximal end 306 of the die 300. In an embodiment, one or more of the mandrels 310, 312, 314, extends to a point that is distal of a proximal end 306 of the die 300. In an embodiment, a proximal end of one of the mandrels 310, 312, 314, engages a distal end of one of the lumens 210, 212, 214 in an interference fit and retains the catheter body section 232 within the die 300. For example a primary mandrel 310 engages a primary lumen 210 of the catheter body 232, a secondary mandrel 312 engages a secondary lumen 212 of the catheter body 232, and a tertiary mandrel 314 engages a tertiary lumen 214 of the catheter body 232. In an embodiment, a cross-sectional shape of the mandrel 310, 312, 314 is equal to, or slightly larger than, a cross-sectional shape of a respective lumen 210, 212, 214 to engage the respective lumen in an interference fit.

Figure 8B:
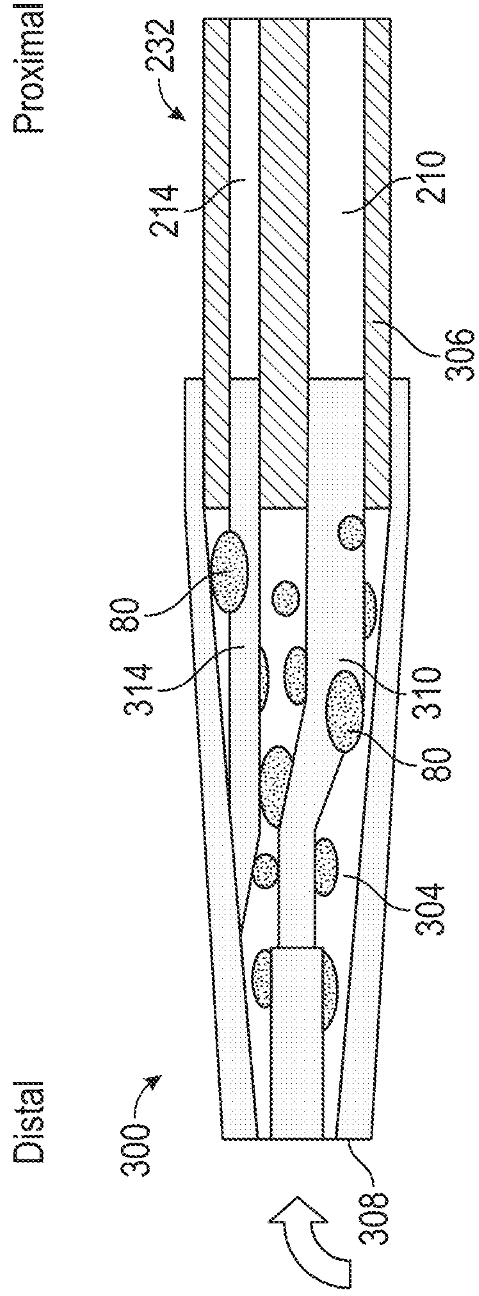

As shown in FIG. 8B, with the proximal end of the catheter body section 232 engaged with the die 300, a material 80, for example one of a first polymeric material, second polymeric material, or a third polymeric material, can be introduced into the cavity 304. The polymeric material can be provided as a single slug, tube, rod, or cylinder of material, or as a powder or granulated material in a flowable, or semi-flowable state. In an embodiment, the material 80 can placed within the cavity 304 before the catheter body 232 engages the catheter section 332 of the die 300. In an embodiment, the material 80 can be introduced into the cavity 304 after the catheter body 232 engages the catheter section 332 of the die 300. For example through a distal end 306 of the die 300 or through a dedicated lumen extending through a wall of the die body 302 and communicating with the cavity 304.

Figures 8C, 8D:
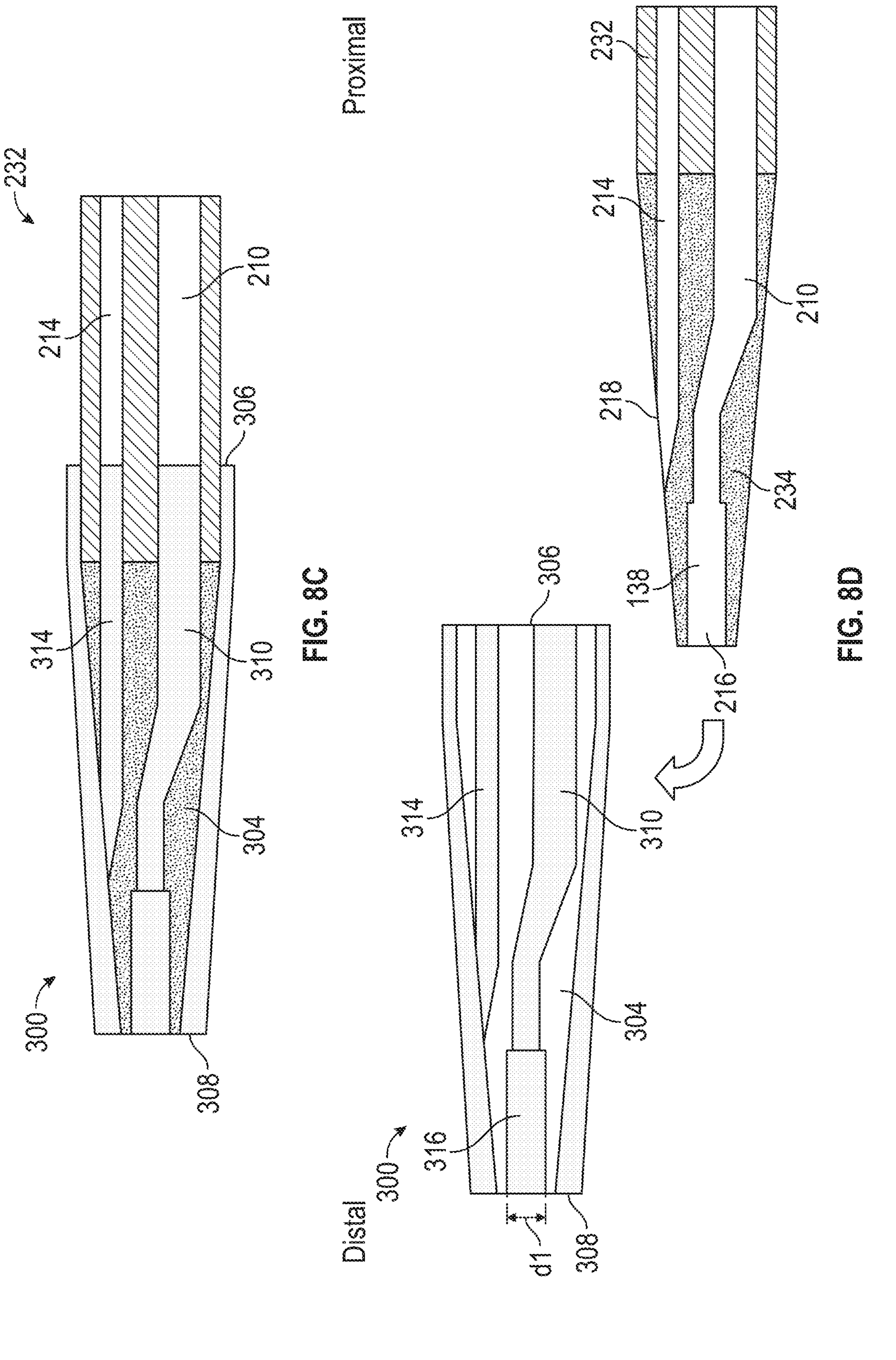

As shown in FIG. 8C, energy (RF energy, thermal energy, or the like) can be applied to the material 80 within the cavity 304 of the die 300 to melt the material 80 and form the catheter tip. The material 80 can conform to the shape of the cavity 304 and can conform around the mandrels 310, 312, 314. Further the material 80 can fuse with a distal end of the catheter body 232. As such, the material 80 is formed into a dilator section 234 of the RICC 202 and coupled with the distal end of the catheter body 232. Further, the join between transition section 234 and the catheter body 232 provides a smooth abluminal surface.

As shown in FIGS. 8C-8D, once the material 80 has been conformed to the shape of the cavity 304, the material 80 can be set or cured to maintain the shape. The die body 302 and the one or more mandrels 310, 312, 314 can then be removed providing the dilator section 234 coupled with the catheter body section 232 and forming a continuous abluminal surface. Further, a portion of one of the primary lumen 210, secondary lumen 212, or tertiary lumen 214 can be formed extending through the dilator section 234.

In an embodiment, the cavity 304 of the die can define the access section 230, or at least a portion of the access section 302, of the RICC 202. As such, the material 80, which can include the first material, second material, or third material, can be injected into the cavity 304, as described herein to form both the dilator section 234 and the access section 230.

In an embodiment, a diameter of the distal end 306 of the cavity 304 can be equal to an outer diameter (d1) of the access section 230. Further, an outer diameter of the distal end of the primary mandrel 310 can be equal to an inner diameter of the primary lumen 210. As such an access section 230 can be coupled with a distal end of the dilator section 234 by adhering, bonding, welding, or the like. In an embodiment, the primary mandrel 310 can include a collar portion 316. In an embodiment, the outer diameter of the collar 316 of the primary mandrel 310 can be equal to an outer diameter (d1) of the access section 230.

Figures 8E, 8F:
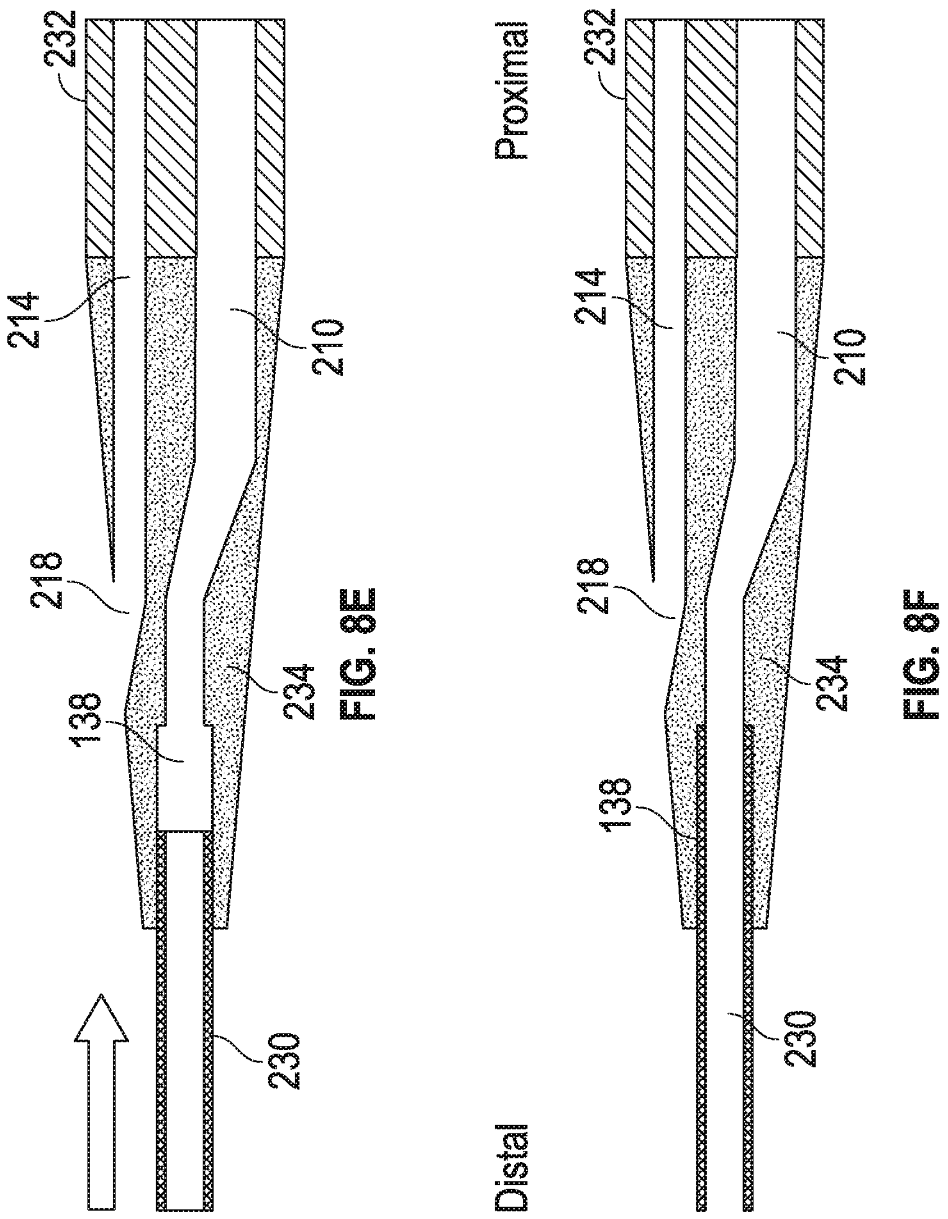

As such, as shown in FIGS. 8E-8F, a proximal end of the access section 230 can be inserted into a receptacle 138 formed in a distal end of the dilator section 234 and can be secured therein using adhesive, bonding, welding, or the like, as described herein. As noted, the access section 230 and the dilator section 234 can be formed of the same material and can be formed integrally within the die as a single monolithic piece and coupled to the catheter body 232. In an embodiment, the access section 230 and the dilator section 234 can be formed of the same material and can be coupled together, e.g. within the receptacle 138, using adhesive, bonding, welding, or the like, as described herein. In an embodiment, the access section 230 and the dilator section 234 can be formed of different materials and can be coupled together, e.g. within the receptacle 138, using adhesive, bonding, welding, or the like, as described herein. In an embodiment, an insertion aperture 122 can be formed in a distal portion of the catheter body 232 and communicate with the primary lumen 210.

Advantageously, methods described herein can form one or both of the secondary lumen aperture 218 or the tertiary lumen aperture 220 within the same step as forming the dilator section 234. This can remove the need for forming (e.g. machining, milling, skiving, cutting, etc.) the secondary lumen aperture 218 or the tertiary lumen aperture 220 after the formation of the dilator section 234 or after the tipping process, reducing the complexity of manufacturing and reducing associated costs. Further, embodiments, described herein show a method of forming one or both of the secondary lumen aperture 218 or the tertiary lumen aperture 220 at an equal longitudinal distal from a primary lumen aperture 216 and formed within the tapered profile of the dilator section 234 while maintaining a smooth abluminal and/or intra-luminal surface. Further, as shown in FIGS. 8B-8C, the die 300, including one or more of the mandrels 310, 312, 314, extend across the join between the dilator section 234 and the catheter body section 232 providing smooth abluminal and intra-lumina surfaces at the join between these two structures.

An exemplary method of using the system 100 including one of the RICC 102 or RICC 202 includes an insertion site-creating step, a RICC-inserting step, and a RICC-advancing step. The insertion site-creating step includes creating an insertion site to access a vasculature of a patient with the introducer needle 104 disposed within the primary lumen 210 of the RICC 202. The insertion site can be at a subclavian vein such as a right or left subclavian vein, an internal jugular vein such as a right or left internal jugular vein, or a femoral vein.

The RICC-inserting step includes inserting distal portion of the RICC 202 into the insertion site up to past the dilator section 234, disposed between an access section 230 and a catheter body section 232. Optionally, the RICC-inserting step is prefaced by an access guidewire-inserting step and the following needle-withdrawing step. The access guidewire-inserting step includes inserting the access guidewire 106 through the distal end of the introducer needle 104 and into one of the foregoing veins.

The method further includes a needle-withdrawing step. The needle-withdrawing step includes withdrawing the introducer needle 104 from the primary lumen 210 of the RICC 202 after the insertion site-creating step and inserting at least some of the distal portion of the RICC 202 into the insertion site.

The RICC-advancing step includes advancing the distal portion RICC 202 through the vasculature of the patient without use of a Seldinger technique. For example, if the insertion site is at the right subclavian vein or the right internal jugular vein, the RICC-advancing step can include advancing the distal portion of the RICC 202 through the right subclavian vein or the right internal jugular vein, a right brachiocephalic vein, and into a superior vena cava. Other insertions sites such as at the left subclavian vein or the left internal jugular vein require advancing the distal portion of the RICC 202 through corresponding vasculature. Optionally, the RICC-advancing step is prefaced by a maneuver guidewire-inserting step of inserting the placement guidewire 108 through the distal end of the RICC 202 and to a target location (e.g., superior vena cava).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of forming a rapidly insertable central catheter, comprising:

providing a catheter body having a primary lumen, a secondary lumen and a tertiary lumen, each extending longitudinally;

placing a distal end of the catheter body within a die, the die having a first mandrel engaging the primary lumen, a second mandrel engaging the secondary lumen, and a third mandrel engaging the tertiary lumen; and melting a polymeric material disposed within a cavity of the die to form a dilator section coupled to the distal end of the catheter body, the dilator section defining a tapered out profile and including a secondary lumen aperture disposed in a side wall and communicating with the secondary lumen, and a tertiary lumen aperture disposed in the side wall and communicating with the tertiary lumen.

2. The method according to claim 1, further including forming an access section integrally with the dilator section and extending from a distal end thereof, the access section defining a single lumen communicating with the primary lumen and extending to a primary lumen aperture disposed at a distal tip thereof.

3. The method according to claim 2, wherein the access section and the dilator section are formed of a first polymeric material and the catheter body is formed of a second polymeric material, the first polymeric material displaying a harder durometer relative to the second polymeric material.

4. The method according to claim 1, wherein the first mandrel includes a collar disposed at a distal end thereof, the collar defining an outer diameter equal to an outer diameter of an access section.

5. The method according to claim 4, further including placing a proximal end of the access section within a receptacle of the dilator section, defined by the collar of the first mandrel and securing the access section to the dilator section using adhesive, bonding, solvent bonding, or welding.

6. The method according to claim 5, wherein the access section is formed of a first polymeric material and the catheter body is formed of a second polymeric material, the first polymeric material displaying a harder durometer relative to the second polymeric material.

7. The method according to claim 6, wherein the dilator section is formed of one of the first polymeric material, the second polymeric material, or a third polymeric material having a harder durometer relative to the second polymeric material and a softer durometer relative to the first polymeric material.

8. The method according to claim 1, wherein the melting further includes applying one of radio frequency (RF) energy or thermal energy to melt the polymeric material.

9. The method according to claim 1, wherein one or both of the secondary lumen aperture and the tertiary lumen aperture are disposed in a longitudinal mid-point of the dilator section between a proximal end and the distal end.

10. The method according to claim 1, wherein the secondary lumen aperture and the tertiary lumen aperture are disposed at an equal longitudinal length relative to a distal tip of the rapidly insertable central catheter.

11. The method according to claim 1, further including forming an introducing aperture disposed proximally of one or both of the secondary lumen aperture and the tertiary lumen aperture and communicating with the primary lumen, the introducing aperture configured to receive an access needle therethrough, a distal tip of the access needle extending through a primal lumen aperture disposed at a distal tip of the rapidly insertable central catheter.

12. The method according to claim 1, wherein providing the catheter body further includes extruding or trimming the catheter body section to a predetermined length and coupling a proximal end of the catheter body to one or more of a catheter hub and one or more extension legs.

* * * * *